US012788722B2

(12) United States Patent
Li et al.

(10) Patent No.: US 12,788,722 B2
(45) Date of Patent: Nov. 10, 2026

(54) ENTERIC-COATED PELLET, METHOD FOR PREPARING SAME AND FORMULATION COMPRISING SAME

(71) Applicant: LIVZON PHARMACEUTICAL GROUP INC., Zhuhai (CN)

(72) Inventors: Pucheng Li, Zhuhai (CN); Yating Mo, Zhuhai (CN); Xiangna Zhang, Zhuhai (CN); Xuemei Hou, Zhuhai (CN); Yannan Cui, Zhuhai (CN); Siwen Hu, Zhuhai (CN); Caihua Cheng, Zhuhai (CN); Weishan Lin, Zhuhai (CN); Zengqing Tu, Zhuhai (CN); Yurong Zhang, Zhuhai (CN); Hongdan Shen, Zhuhai (CN); Shenchao Jiao, Zhuhai (CN); Yang Feng, Zhuhai (CN); Zhihui Han, Zhuhai (CN); Lei Wu, Zhuhai (CN); Zhuanxia Zhang, Zhuhai (CN)

(73) Assignee: LIVZON PHARMACEUTICAL GROUP INC., Zhuhai (CN)

( * ) Notice: Subject to any disclaimer, the term of this patent is extended or adjusted under 35 U.S.C. 154(b) by 561 days.

(21) Appl. No.: 18/255,163

(22) PCT Filed: Nov. 12, 2021

(86) PCT No.: PCT/CN2021/130394
§ 371 (c)(1),
(2) Date: May 31, 2023

(87) PCT Pub. No.: WO2022/116796
PCT Pub. Date: Jun. 9, 2022

(65) Prior Publication Data
US 2024/0033224 A1 Feb. 1, 2024

(51) Int. Cl.
*A61K 9/28* (2006.01)
*A61K 9/20* (2006.01)
*A61K 31/4439* (2006.01)

(52) U.S. Cl.
CPC .......... *A61K 9/2853* (2013.01); *A61K 9/2018* (2013.01); *A61K 9/2054* (2013.01);
(Continued)

(58) Field of Classification Search
CPC ............................ A61K 9/2853; A61K 9/5073
See application file for complete search history.

(56) References Cited

U.S. PATENT DOCUMENTS 4,786,505 A 11/1988 Lovgren et al.
6,280,773 B1 8/2001 Cho et al.

FOREIGN PATENT DOCUMENTS

CN 87103285 A 11/1987
CN 1146720 A 4/1997
(Continued)

OTHER PUBLICATIONS

Espacenet Machine Translation of CN 103405462 A (Hou, X. et al.) published Nov. 27, 2013. Accessed Jul. 3, 2025. (Year: 2013).*
(Continued)

*Primary Examiner* — Carlos A Azpuru
(74) *Attorney, Agent, or Firm* — NKL Law; Allen Xue

(57) ABSTRACT

An enteric-coated pellet, a method for preparing the same and a formulation comprising the same are provided. The enteric-coated pellet can be an ilaprazole enteric-coated pellet.

13 Claims, 6 Drawing Sheets

(52) U.S. Cl.
CPC .......... *A61K 9/2059* (2013.01); *A61K 9/2826* (2013.01); *A61K 31/4439* (2013.01)

(56) References Cited

FOREIGN PATENT DOCUMENTS

| | | | | |
|---|---|---|---|---|
| CN | 1183047 | A | | 5/1998 |
| CN | 1785186 | A | | 6/2006 |
| CN | 101036633 | A | | 9/2007 |
| CN | 102119927 | A | | 7/2011 |
| CN | 102255219 | A | * | 7/2012 |
| CN | 102525990 | A | | 7/2012 |
| CN | 102552190 | A | | 7/2012 |
| CN | 102552214 | A | | 7/2012 |
| CN | 102552256 | A | | 7/2012 |
| CN | 103340829 | A | | 10/2013 |
| CN | 103405462 | A | | 11/2013 |
| CN | 103432149 | A | | 12/2013 |
| CN | 103705483 | A | | 4/2014 |
| CN | 104586772 | A | | 5/2015 |
| CN | 106176669 | A | | 12/2016 |
| CN | 114569575 | A | * | 6/2022 |
| CN | 114569579 | A | * | 6/2022 |
| EP | 0244380 | A2 | | 11/1987 |
| EP | 0519365 | A1 | | 12/1992 |
| JP | H05194225 | A | | 8/1993 |
| JP | H05294831 | A | | 11/1993 |
| JP | H0733659 | A | | 2/1995 |
| JP | 2009519943 | A | | 5/2009 |
| JP | 2018118936 | A | | 8/2018 |
| SG | 103334 | A1 | | 4/2004 |
| WO | 2008057802 | A2 | | 5/2008 |
| WO | 2008083319 | A1 | | 7/2008 |
| WO | 2023025231 | A1 | | 3/2023 |

OTHER PUBLICATIONS

Li, Zhiqing et al.; "To evaluate the clinical efficacy and safety of ilaprazole enteric-coated tablet in the patients with duodenal ulcer"; Anti Infect Pharm; vol. 16, No. 5; May 6, 2019; Issn 1672-7878/CN 32-1726/R; pp. 912-913.

Divya, B et al.; "Development of Extended Release Formulations of llaprazole Tablets.", Journal of Drug Delivery and Therapeutics .; vol. 9, No. 3; May 15, 2019; pp. 8-12.

* cited by examiner

ENTERIC-COATED PELLET, METHOD FOR PREPARING SAME AND FORMULATION COMPRISING SAME

CROSS-REFERENCE TO RELATED APPLICATIONS

This application is a U.S. national stage entry of PCT International Application No. PCT/CN2021/130394, filed on Nov. 12, 2021, which claims the priority to Chinese Patent Application No. 202011391266.5 filed with the China National Intellectual Property Administration on Dec. 2, 2020, the content of which is incorporated herein by reference in its entirety.

TECHNICAL FIELD

The present invention relates to an enteric-coated pellet, a method for preparing the same and a formulation comprising the same, and in particular to an ilaprazole enteric-coated pellet, a method for preparing the same and a formulation comprising the same.

BACKGROUND

Proton Pump Inhibitor (PPI) is a drug capable of selectively inhibiting the $H^+/K^+$-ATPase (also known as proton pump or acid pump) on the secretory canalicular membrane of human gastric mucosal cells. Since the $H^+/K^+$-ATPase is the final pathway for the inhibition of gastric acid secretion, the inhibition of which significantly reduces gastric acid secretion, the proton pump inhibitor is commonly used to treat diseases of the digestive tract induced or caused by the action of gastric acid (i.e., acid-related diseases), including gastric and duodenal ulcers, gastroesophageal reflux disease, surgical stomal ulcers, zollinger-ellison syndrome, and the like. Known PPIs can be classified into non-reversible PPIs and reversible PPIs (RPPIs) according to the mechanism of action. Among them, the non-reversible PPIs are mainly benzimidazole derivatives, can rapidly pass through the parietal cell membrane and accumulate in a strongly acidic secretory canaliculus, and then are protonated and converted into sulfenamide compounds which can form a covalently bound disulfide bond with a sulfhydryl group on a cysteine residue in the $H^+/K^+$-ATPase a subunit, thereby irreversibly inactivating the $H^+/K^+$-ATPase and inhibiting its acid secretion activity (Zhangxuan, "Review of Proton Pump Inhibitor—Prazoles Pharmaceutical Patent Technology", *Patent Document Research* (2018)—*Pharmaceutical Medicine*, Intellectual Property Publishing House, Beijing, 2019.9: p 554-567). Such drugs currently on the market globally include omeprazole, lansoprazole, pantoprazole, rabeprazole, esomeprazole, ilaprazole, delansoprazole, and the like.

Similar to other prazoles, ilaprazole is also an acid labile compound. However, ilaprazole has a lower stability than other currently available prazoles. Acid labile compounds are substances that are unstable in acidic media but have better stability in neutral and alkaline media. These compounds have the common feature that they become biologically effective compounds through rapid degradation/transformation in acid media. Acid labile proton pump inhibitors are susceptible to degradation/transformation in acidic and neutral media and should be protected from the contact with gastric acid to affect their stability when administered orally. A conventional approach to solve this problem is to coat oral formulations of such drugs with an enteric-coated material to obtain enteric-coated pellet formulations (for example, see CN 1183047 A, CN 1146720 A, U.S. Pat. No. 4,786,505 and EP 0519365). These enteric-coated pellet formulations generally comprise a pellet core, a buffer coating layer and an outer enteric coating layer. For the pellet core, an alkalizing agent (also known as a buffer) may be added to the pharmaceutical composition of the pellet core to increase the stability of the PPIs, or an alkaline layer may be added to the pellet core without the alkalizing agent to protect the PPIs from acid damage (see CN 103705483 A). In addition, in order to avoid the effect of the free carboxyl group in the enteric-coated material on the stability of such drugs, a buffer coating layer (i.e., an isolating layer) with a certain thickness is required inside the enteric coating layer.

With regard to the isolating layer, a number of technical solutions have been disclosed in the prior art, for example:

CN 87103285 A (Chinese patent family member of the above-mentioned U.S. Pat. No. 4,786,505) discloses a pharmaceutical formulation of an acid labile substance (e.g., a benzimidazole compound) for oral administration. The pharmaceutical formulation for treating gastrointestinal diseases consists of a core material, one or more subcoating layers (i.e., isolating layers) and an enteric coating layer, wherein the core material comprises an acid labile compound and an alkaline reacting compound, or comprises a selective alkaline salt of an acid labile compound and an alkaline compound; the subcoating layer comprises an inert reacting compound which is soluble or rapidly disintegrable in water, or a film-forming polymeric compound which is soluble in water, and optionally may also comprise an alkaline compound for buffering pH. In addition, the final enteric-coated dosage form is treated in a suitable manner to reduce the moisture content to a very low level so as to obtain a dosage form with a good stability in long-term storage. The alkaline compound for buffering pH may be magnesium oxide, magnesium hydroxide or magnesium carbonate, aluminum hydroxide or calcium hydroxide, aluminum carbonate or calcium carbonate, aluminum silicate or calcium silicate; complex aluminum/magnesium compounds, for example, $Al_2O_3\cdot 6MgO\cdot CO_2\cdot 12H_2O$, $(Mg_6Al_2(OH)_{16}CO_3\cdot 4H_2O)$, or $MgO\cdot Al_2O_3\cdot 2SiO_2\cdot nH_2O$, wherein n is not an integer and is less than 2, or similar compounds; or other pharmaceutically acceptable pH-buffering substances, for example, sodium, potassium, calcium, magnesium and aluminum salts of phosphoric acid, citric acid or other suitable weak inorganic or organic acids. The material used for the isolating layer is selected from pharmaceutically acceptable water-soluble inert compounds or polymers used as coating films, for example, saccharide, polyethylene glycol, polyvinylpyrrolidone, polyvinyl alcohol, hydroxypropylcellulose, hydroxymethylcellulose, hydroxypropyl methylcellulose and the like. In the isolating layer, conventional plasticizers, pigments, titanium dioxide, talc and other additives may also be included.

CN 101036633 A discloses an omeprazole enteric-coated pellet capsule and a method for preparing the same. The content of this capsule is an omeprazole enteric-coated pellet, which comprises a blank pellet core, an active drug layer comprising an alkaline ingredient, an isolating layer and an enteric coating layer. The isolating layer isolates the alkaline active drug layer of omeprazole from an acidic enteric-coated material, and is added with magnesium oxide and titanium dioxide as protective ingredients simultaneously, so that the stability of the drug is significantly improved through the synergistic effect.

CN 102119927 A discloses a proton pump inhibitor enteric-coated pellet formulation and a method for preparing the same. The proton pump inhibitor enteric-coated pellet consists of a blank pellet core, a drug-loading layer, isolating layers (I) and (II) and an enteric coating layer. In order to increase the drug stability and improve the drug-loading efficiency reduced by adding water-insoluble alkali, the drug-loading layer and the isolating layer (I) both comprise water-soluble inorganic alkali, and the alkali used in the drug-loading layer comprises sodium hydroxide and another water-soluble inorganic alkali which can form a buffer and an alkaline environment a pH of 11-12 (excluding 11) with the sodium hydroxide in an aqueous solution.

CN 106176669 A discloses a pantoprazole sodium enteric-coated pellet, a method for preparing the same, a capsule comprising the pellet and a method for preparing the capsule, wherein the pantoprazole sodium enteric-coated pellet comprises a pellet core, a first isolating layer, a second isolating layer and an enteric coating layer in sequence from inside to outside, wherein the pellet core comprises pantoprazole sodium and a composite alkaline substance (a mixture of sodium phosphates); the first isolating layer comprises hydroxypropyl methylcellulose, povidone k30, polyethylene glycol 600 (PEG-600), magnesium stearate and talc; the second isolating layer comprises hydroxypropyl methylcellulose, polyethylene glycol 400 (PEG-400), sodium bicarbonate, titanium dioxide and glycerol triacetate; and in the enteric-coated pellet, the mass ratio of the first isolating layer to the second isolating layer can significantly affect the final efficacy.

CN 1785186 A discloses an enteric-coated pellet of pantoprazole or salts thereof, which comprises a pellet core, a subcoating layer, a drug layer, a buffer layer, an isolating layer and an enteric coating layer from inside to outside. In order to obtain a desired effect, the number of coating layers, the thickness of each layer, the amount of an intermediate layer adhesive and stabilizer, etc., must be adjusted, and thus the increase in weight of each layer is strictly limited in this document, otherwise the desired effect of this invention cannot be achieved.

The method for preparing a prazole enteric-coated pellet and a formulation thereof in the prior art has the following disadvantages, which results in the failure of having both the good stability and the acid resistance (especially the acid resistance is not easily satisfied) for the prazole enteric-coated pellet and the formulation thereof in the prior art: in the isolating layers of the prazole enteric-coated pellet prepared by the prior art, the isolating layer closely adjacent to the pellet core (i.e., a drug-containing pellet) usually comprises water-insoluble inert substances capable of preventing the pellet from adhesion (such as talc, silica, titanium dioxide and magnesium stearate) and/or water-soluble alkaline compounds, and the isolating layer closely adjacent to the enteric coating layer usually comprises alkaline compounds, both of which will reduce the stability and/or acid resistance of the enteric-coated pellet and the formulation thereof.

SUMMARY

Therefore, one of the objectives of the present invention is to provide an ilaprazole enteric-coated pellet, which overcomes the drawbacks of the prior art, and can have one, two or more of the following properties: good stability, good acid resistance, increased dissolution and/or increased drug-loading rate (sometimes also referred to herein as drug-applying rate) and bioavailability.

The above objective is achieved by the enteric-coated pellet according to the present invention, which comprises a pellet core, a first isolating layer, a second isolating layer and an enteric coating layer in sequence from inside to outside, wherein the pellet core comprises ilaprazole and/or a pharmaceutically acceptable salt of ilaprazole and a first excipient.

According to a first aspect of the present invention, provided is an enteric-coated pellet, comprising a pellet core, a first isolating layer, a second isolating layer and an enteric coating layer in sequence from inside to outside, wherein the pellet core comprises ilaprazole and/or a pharmaceutically acceptable salt of ilaprazole and a first excipient, and the enteric-coated pellet is characterized in that the first isolating layer comprises a water-insoluble alkaline compound, and the weight ratio of the first excipient to ilaprazole and/or the pharmaceutically acceptable salt of ilaprazole is 0.2:1-5:1.

According to a second aspect of the present invention, provided is an enteric-coated pellet, comprising a pellet core, a first isolating layer, a second isolating layer and an enteric coating layer in sequence from inside to outside, wherein the pellet core comprises ilaprazole and/or a pharmaceutically acceptable salt of ilaprazole and a first excipient, and the enteric-coated pellet is characterized in that the first isolating layer comprises a water-insoluble alkaline compound, and the first excipient is a water-insoluble alkaline compound, wherein the water-insoluble alkaline compound comprised in the first isolating layer and the water-insoluble alkaline compound of the first excipient can be the same or different.

According to a third aspect of the present invention, provided is an enteric-coated pellet, comprising a pellet core, a first isolating layer, a second isolating layer and an enteric coating layer in sequence from inside to outside, wherein the pellet core comprises ilaprazole and/or a pharmaceutically acceptable salt of ilaprazole and a first excipient, and the enteric-coated pellet is characterized in that a particle size D90 of ilaprazole and/or the pharmaceutically acceptable salt of ilaprazole is less than or equal to 100 μm, and the second isolating layer does not comprise an alkaline substance.

According to an embodiment of the present invention, a protective layer is further provided outside the enteric coating layer of the enteric-coated pellet according to the present invention.

According to an embodiment of the present invention, in the enteric-coated pellet according to the present invention, no other layer is present between the pellet core and the first isolating layer.

According to an embodiment of the present invention, in the enteric-coated pellet according to the present invention, no other layer is present between the second isolating layer and the enteric coating layer.

According to an embodiment of the present invention, in the enteric-coated pellet according to the present invention, no other layer is present between the first isolating layer and the second isolating layer.

According to an embodiment of the present invention, the first excipient of the enteric-coated pellet according to the present invention is an alkaline compound, preferably a water-insoluble alkaline compound, and more preferably selected from magnesium hydroxide, aluminum hydroxide, magnesium oxide, magnesium carbonate, calcium carbonate and calcium hydroxide.

According to an embodiment of the present invention, the pharmaceutically acceptable salt of ilaprazole may be, for example, ilaprazole sodium, ilaprazole magnesium, ilaprazole zinc, ilaprazole potassium, ilaprazole lithium or ilaprazole calcium and the like. Herein, those skilled in the art can select a suitable salt as needed.

According to an embodiment of the present invention, the pellet core of the enteric-coated pellet according to the present invention further comprises a surfactant. Preferably, the surfactant is tween-80 or sodium dodecyl sulfate.

According to an embodiment of the present invention, the weight ratio of the water-insoluble alkaline compound in the first isolating layer to ilaprazole and/or the pharmaceutically acceptable salt thereof is 0.2:1-5:1, preferably 0.25:1-4:1, more preferably 0.3:1-3:1, particularly preferably 0.5:1-2:1, and most preferably 0.8:1-1.2:1, for example, 1:1.

According to an embodiment of the present invention, the second isolating layer comprises a water-insoluble inert substance capable of preventing the adhesion of the pellets, and the weight ratio of the water-insoluble inert substance to the binder is 1-8:1.5-10, 1-10:1-20, or 4-26:7-44.

According to an embodiment of the present invention, the particle size D90 of ilaprazole and/or the pharmaceutically acceptable salt of ilaprazole may be in a range selected from the ranges between any two of the following endpoints: 0 μm (excluding this value when forming a range), 10 μm, 20 μm, 30 μm, 40 μm, 50 μm, 60 μm, 70 μm, 80 μm, 90 μm, and 100 μm.

It will be understood by those skilled in the art that one or more features of the various aspects and embodiments herein may be freely combined to form new technical solutions, and that technical solutions obtained by those combinations also fall within the scope of the present invention. The technical solutions, terms and principles of the present invention will be further explained below.

Pellet Core of Enteric-Coated Pellet

The pellet core (or known as a drug-containing pellet) of the enteric-coated pellet according to the present invention may be a fully-active pellet core or a blank pellet core coated with a drug-loading layer. The term "fully-active pellet core" used herein refers to a pellet core comprising ilaprazole and/or a pharmaceutically acceptable salt of ilaprazole and a first excipient, and other pharmaceutically acceptable excipient(s), wherein ilaprazole and/or the pharmaceutically acceptable salt of ilaprazole as an active ingredient is dispersed in the other ingredients (the first excipient and other pharmaceutically acceptable excipient(s), etc.) without forming another layer independently or together with any other ingredients; in the blank pellet core coated with a drug-loading layer, the drug-loading layer comprises ilaprazole and/or a pharmaceutically acceptable salt of ilaprazole and a first excipient and optionally an excipient.

When ilaprazole and/or the pharmaceutically acceptable salt thereof in the pellet core cannot achieve sufficient storage stability only under the action of the water-insoluble alkaline compound comprised in a first isolating layer, the first excipient additionally added to the pellet core can achieve an improvement in storage stability of the ilaprazole and/or the pharmaceutically acceptable salt thereof. The first excipient in the pellet core may be a conventional excipient used in the prior art for improving the stability of acid labile compounds. Preferably, the first excipient is an alkaline compound, comprising a water-insoluble alkaline compound and a water-soluble alkaline compound. Preferably, according to the present invention, a water-insoluble alkaline compound is used as the first excipient in the pellet core; more preferably, the water-insoluble alkaline compound comprised in the pellet core is the same as the water-insoluble alkaline compound comprised in the first isolating layer, thereby further enhancing the effect of the isolating layer in buffering pH. In an embodiment according to the present invention, the water-insoluble alkaline compound may be selected from, but is not limited to, one or more of magnesium hydroxide, aluminum hydroxide, magnesium oxide, magnesium carbonate, calcium carbonate and calcium hydroxide. Preferably, the weight ratio of the alkaline compound to ilaprazole and/or the pharmaceutically acceptable salt thereof is 0.2:1-5:1, preferably 0.25:1-4:1, more preferably 0.3:1-3:1, particularly preferably 0.5:1-2:1, and most preferably 0.8:1-1.2:1, for example, 1:1.

According to the present invention, the pellet core may further comprise a surfactant. The results of the examples of the present invention demonstrate that the surfactant can improve the dissolution rate of ilaprazole and/or the pharmaceutically acceptable salt thereof in the enteric-coated pellet and the formulation thereof, thereby effectively improving the bioavailability of ilaprazole and/or the pharmaceutically acceptable salt thereof. In an embodiment according to the present invention, the surfactant comprised in the pellet core may be selected from a nonionic surfactant, an anionic surfactant and a zwitterionic surfactant. Preferably, the nonionic surfactant may be selected from polyethylene glycols, polyhydric alcohols (such as tween-80) and the like; the anionic surfactant may be selected from higher fatty acid salts, sulfuric ester salts, sulfonates and the like, such as sodium dodecyl sulfate; and the zwitterionic surfactant may be selected from phosphate esters.

According to the present invention, the particle size of ilaprazole and/or the pharmaceutically acceptable salt thereof can affect the dissolution rate and/or drug-loading rate of the enteric-coated pellet. In a preferred embodiment according to the present invention, ilaprazole and/or the pharmaceutically acceptable salt thereof may have a particle size D90 less than or equal to 100 m; in this case, the enteric-coated pellet has good dissolution rate, so that the bioavailability of the enteric-coated pellet formulation prepared from the enteric-coated pellet can be improved. More preferably, ilaprazole and/or the pharmaceutically acceptable salt thereof may have a particle size D90 in a range selected from the ranges between any two of the following endpoints: 10 μm, 20 μm, 30 μm, 40 μm, 50 μm, 60 μm, 70 μm, 80 μm, 90 μm, and 100 μm, and especially a particle size D90 less than or equal to 50 μm, so that an improved drug-loading rate can be achieved.

According to an embodiment of the present invention, the above blank pellet core is a blank pellet core conventionally used in the prior art. In an embodiment according to the present invention, the blank pellet core may be selected from, but is not limited to, a microcrystalline cellulose pellet core, a sucrose pellet core and a mannitol pellet core, and may have a particle size of 50-500 μm, preferably 100-400 μm, more preferably 250-350 μm, and most preferably about 300 μm.

According to an embodiment of the present invention, the drug-loading layer described above may further comprise a binder. The binder may be selected from, but is not limited to, one or more of hydroxypropylcellulose, hydroxypropyl methylcellulose, hydroxymethylcellulose, hydroxyethylcellulose, carboxymethylcellulose, methylcellulose, polyvinyl pyrrolidone, polyvinyl alcohol, polyethylene glycol, syrup, and starch. In an embodiment according to the present invention, the binder may be selected from one or more of hydroxypropylcellulose-SSL (e.g., commercially available series from Nisso), hydroxypropyl methylcellulose-E5, polyvinylpyrrolidone K30, polyvinyl alcohol, methylcellulose and polyethylene glycol.

Isolating Layers of Enteric-Coated Pellet

The isolating layers of the enteric-coated pellet generally function to isolate the pellet core in an alkaline environment from the enteric coating layer comprising free carboxyl groups to prevent the degradation or discoloration of ilaprazole and/or the pharmaceutically acceptable salt thereof during the coating or storage. In the research on the ilaprazole enteric-coated pellet and the formulation thereof, the inventors have found that, the use of water-insoluble inert substances capable of preventing the pellet from adhesion (such as talc, silica, titanium dioxide and magnesium stearate) and/or water-soluble alkaline compounds, which are commonly used in the conventional preparation methods in the prior art (for example, when an isolating layer closely adjacent to the pellet core is prepared), and alkaline compounds, which are commonly used when an isolating layer closely adjacent to the enteric coating layer is prepared, can reduce the stability and/or acid resistance of the enteric-coated pellet and the formulation thereof, especially for acid labile compounds with relatively low stability such as ilaprazole, which will result in that the enteric-coated pellet and the formulation thereof cannot simultaneously meet the requirements on the stability and acid resistance. The term "closely adjacent" used herein means that no other layer is present between the pellet core of the enteric-coated pellet and coating or covering layers thereof or between the two layers.

One of the causes of this technical problem, which the inventors have experimentally demonstrated and believed, without being limited thereto, is that the compatibility between the water-insoluble inert substance capable of preventing the pellet from adhesion and comprised in the isolating layer closely adjacent to the pellet core (corresponding to the first isolating layer according to the present invention) and the acid labile compound comprised in the pellet core differs due to the different stability of the acid labile compound, that is, in the enteric-coated pellet and the formulation thereof prepared according to the prior art, when the stability of the acid labile compound comprised in the pellet core (e.g., ilaprazole) is low, the compatibility between the water-insoluble inert substance capable of preventing the pellet from adhesion and comprised in the isolating layer closely adjacent to the pellet core (e.g., talc) and the acid labile compound is reduced accordingly. Therefore, even under the protection of the alkaline compound comprised in the pellet core and/or the isolating layers as a stabilizer, a significant increase of relevant substances (i.e., impurities) in the accelerated test results is caused, thereby decreasing the stability of the enteric-coated pellet formulation. This limits to some extent the range of acid labile compounds that can be suitable for use in enteric-coated pellets and formulations thereof prepared according to the prior art, that is, the prescriptions or compositions of enteric-coated pellets and formulations thereof prepared according to the prior art cannot be well suitable for use in ilaprazole and/or a pharmaceutically acceptable salt thereof with a relatively low stability. In addition, when the water-soluble alkaline compound is comprised in the isolating layer closely adjacent to the pellet core (corresponding to the first isolating layer according to the present invention), the isolating layer of the enteric-coated pellet absorbs free water under long-term high-temperature and high-humidity conditions to cause the dissolution of the water-soluble alkaline compound, so that the isolating layer closely adjacent to the enteric coating layer has an increased alkalinity and shows alkalinity, and when water is infiltrated into the enteric coating layer in an acidic medium, the enteric coating layer is caused to dissolve in advance, thereby causing a decrease in acid resistance of the enteric-coated pellet and the formulation thereof. The principle that the enteric coating layer is dissolved in advance because the isolating layer closely adjacent to the enteric coating layer shows alkalinity is also applicable to the case where an alkaline compound is comprised in the isolating layer closely adjacent to the enteric coating layer (corresponding to the second isolating layer according to the present invention).

Thus, according to the present invention, the enteric-coated pellet comprises at least two isolating layers comprising an inert substance, i.e., at least a first isolating layer close to and closely adjacent to the pellet core and a second isolating layer away from the pellet core compared with the first isolating layer or closely adjacent to the enteric coating layer, wherein the first isolating layer comprises a water-insoluble alkaline compound and does not comprise a water-soluble alkaline compound and a water-insoluble inert substance capable of preventing the pellet from adhesion, and the second isolating layer does not comprise an alkaline compound. When the enteric-coated pellet comprises three or more isolating layers, the other isolating layer positioned between the first isolating layer and the second isolating layer may be an isolating layer conforming to the definition of the first isolating layer or the second isolating layer according to the present invention, or may be an isolating layer commonly used in the art.

According to the present invention, the water-insoluble alkaline compound may be a water-insoluble alkaline compound commonly used in the art for improving the stability of the acid labile compound.

In an embodiment according to the present invention, the water-insoluble alkaline compound may be selected from, but is not limited to, one or more of magnesium hydroxide, aluminum hydroxide, magnesium oxide, magnesium carbonate, calcium carbonate and calcium hydroxide.

According to the present invention, the water-insoluble inert substance capable of preventing the pellet from adhesion may be selected from one or more of lubricants, glidants and anti-adherents (i.e., anti-sticking agents, the same below) conventionally used in Pharmacy. In an embodiment according to the present invention, the water-insoluble inert substance capable of preventing the pellet from adhesion may be selected from, but is not limited to, silica, calcium silicate, colloidal silica, aluminum silicate, calcium aluminum silicate, magnesium silicate, sodium stearate, zinc stearate, magnesium stearate, talc, titanium dioxide and the like. In an embodiment of the ilaprazole enteric-coated pellet according to the present invention, the first isolating layer of the enteric-coated pellet does not comprise one or more of the following water-insoluble inert substances capable of preventing the pellet from adhesion: talc, silica, titanium dioxide and magnesium stearate.

In a preferred embodiment according to the present invention, the first isolating layer mainly consists of a water-insoluble alkaline compound and a binder, and the second isolating layer mainly consists of a water-insoluble inert substance capable of preventing the pellet from adhesion and a binder. According to the present invention, by adjusting the amount of the water-insoluble alkaline compound and the binder comprised in the first isolating layer or the amount of the water-insoluble inert substance capable of preventing the pellet from adhesion and the binder comprised in the second isolating layer, the dissolution rate of the enteric-coated pellet formulation can be affected, and thus the bioavailability thereof can be affected. For example, in a preferred embodiment of the ilaprazole enteric-coated pellet tablet according to the present invention, the proportion of the components may be as follows: when the amount of ilaprazole is 5-15 parts by weight, the first isolating layer comprises 5-36 parts by weight of a binder and 5-36 parts by weight of a water-insoluble alkaline compound; and the second isolating layer comprises 4-26 parts by weight of a binder and 7-44 parts by weight of a water-insoluble inert substance capable of preventing the pellet from adhesion.

The above binders are those commonly used in the isolating layers according to the prior art. According to the present invention, the binders may be selected from pharmaceutically acceptable water-soluble inert compounds or polymers used as coatings, such as one or more of hydroxypropylcellulose, hydroxypropyl methylcellulose, hydroxymethylcellulose, hydroxyethylcellulose, carboxymethylcellulose, methylcellulose, polyvinyl pyrrolidone, polyvinyl alcohol, polyethylene glycol, syrup and starch.

Enteric Coating Layer of Enteric-Coated Pellet

The enteric coating layers commonly used in the enteric-coated pellet formulations of the prior art are also suitable for use in the present invention, for example, the detailed description of enteric coating layers is recited in CN 87103285 A (Chinese patent family member of U.S. Pat. No. 4,786,505); the inventors take this as a reference and incorporate the disclosure of the document in relation to the enteric coating layer and the disclosure of all documents cited therein into the present application.

According to the present invention, the enteric coating layer may comprise one or more substances selected from the followings: enteric coating materials such as acrylic resins, celluloses such as hydroxymethyl ethylcellulose and Opadry, and optionally one or more additives selected from plasticizers, anti-adherents and lubricants. In an embodiment according to the present invention, the enteric coating layer may comprise an acrylic resin-based enteric coating material, a plasticizer (such as polyethylene glycol, triacetin, triethyl citrate, or phthalate), and an anti-adherent (such as talc, or glyceryl monostearate). The acrylic resin-based enteric coating material is selected from one or more of cellulose acetate phthalate, hydroxypropyl methylcellulose phthalate, a solution or dispersion L30D55 of methacrylate copolymer, hydroxypropyl methylcellulose acetate succinate, polyvinyl acetate phthalate and shellac. In a preferred embodiment of the ilaprazole enteric-coated pellet according to the present invention, the weight ratio of the enteric coating material comprised in the enteric coating layer to ilaprazole and/or the pharmaceutically acceptable salt thereof is 2:1-20:1. In a preferred embodiment of the ilaprazole enteric-coated pellet according to the present invention, the weight ratio of the plasticizer to ilaprazole and/or the pharmaceutically acceptable salt thereof is 0.6:1-6:1, preferably 0.8:1-4:1, and more preferably 1:1-2:1.

Protective Layer of Enteric-Coated Pellet

According to the present invention, a protective layer may be further provided outside the enteric coating layer of the enteric-coated pellet, and preferably, the protective layer is closely adjacent to the enteric coating layer. The protective layer can prevent the adhesion that may occur between various semi-finished products/products during the placement before the preparation of a formulation, or during the preparation of the formulation, or during the placement after the preparation of the formulation. In addition, the arrangement of the protective layer can effectively increase the dissolution rate of the enteric-coated pellet, thereby improving the bioavailability of the enteric-coated pellet formulation prepared from the enteric-coated pellet.

In an embodiment according to the present invention, the protective layer may comprise a binder and an anti-adherent. The binder may be selected from one or more of hydroxypropyl methylcellulose, hydroxypropylcellulose, polyvinylpyrrolidone, polyvinyl alcohol, methylcellulose and polyethylene glycol. The anti-adherent may be selected from one or more of talc, magnesium stearate, titanium dioxide and silica.

According to the present invention, the acid resistance of the enteric-coated pellet can be improved by increasing the amount of the anti-adherent in the protective layer. In a preferred embodiment of the ilaprazole enteric-coated pellet according to the present invention, when the amount of ilaprazole and/or the pharmaceutically acceptable salt thereof is 5-15 parts by weight, the amount of the anti-adherent is 0.5-5 parts by weight.

According to a fourth aspect of the present invention, provided is a method for preparing an enteric-coated pellet, comprising at least the following steps: 1) preparing a pellet core comprising ilaprazole and/or a pharmaceutically acceptable salt of ilaprazole and a first excipient; 2) coating a first isolating layer and then coating a second isolating layer; and 3) coating an enteric coating layer.

Preferably, step 2) comprises: preparing a first suspension comprising a water-insoluble alkaline compound and not comprising a water-soluble alkaline compound and a water-insoluble inert substance capable of preventing the pellet from adhesion, and coating the pellet core obtained in step 1) with the first suspension; and preparing a second suspension not comprising an alkaline compound, and coating with the second suspension as the second isolating layer, preferably as the second isolating layer closely adjacent to the enteric coating layer.

Preferably, in step 1), the first excipient and the water-insoluble alkaline compound comprised in the first isolating layer act together to achieve storage stability of ilaprazole and/or the pharmaceutically acceptable salt of ilaprazole.

Preferably, the method for preparing an enteric-coated pellet further comprises step 4): coating a protective layer.

In an embodiment according to the present invention, the method for preparing an enteric-coated pellet may comprise one or more of the following steps:

1) coating a blank pellet core with a drug-loading layer comprising ilaprazole and/or a pharmaceutically acceptable salt of ilaprazole, an alkaline compound as a first excipient and a binder by, for example, a fluidized bed method to obtain a pellet core;
2) coating the pellet core obtained in step 1) with at least a first suspension and a second suspension in sequence from inside to outside to form a first isolating layer and a second isolating layer by, for example, a fluidized bed method, respectively, so as to obtain an isolated pellet, wherein the first suspension comprises a water-insoluble alkaline compound and does not comprise a water-soluble alkaline compound and a water-insoluble inert substance capable of preventing the pellet from adhesion; and the second suspension does not comprise an alkaline compound; and
3) preparing an enteric coating layer suspension of an enteric coating material and a substance selected from one or more of a plasticizer, an anti-adherent, a lubricant and an emulsifier; and coating the isolated pellet obtained in step 2) with the enteric coating layer suspension by, for example, a fluidized bed method to obtain an enteric-coated pellet.

Preferably, the above method for preparing the enteric-coated pellet may further comprise step 4): adding a binder selected from one or more of hydroxypropylcellulose, hydroxypropyl methylcellulose, methylcellulose, polyvinylpyrrolidone, polyvinyl alcohol, carboxymethylcellulose and polyethylene glycol to purified water to obtain a protective layer coating solution, and coating the enteric-coated pellet obtained in step 3) with the protective layer coating solution by, for example, a fluidized bed method to obtain an enteric-coated pellet having a protective layer.

According to the present invention, optionally, the ilaprazole enteric-coated pellet formulation can be prepared by using the above enteric-coated pellet according to the present invention, wherein the dosage form of the enteric-coated pellet formulation may be tablets, capsules, dry suspensions or pills.

According to a fifth aspect of the present invention, provided is an ilaprazole enteric-coated pellet tablet, comprising the enteric-coated pellet according to the present invention and a tableting excipient (a second excipient, to be distinguished from the excipient described in the pellet core of the enteric-coated pellet).

Optionally, the enteric-coated pellet tablet further comprises a film coating.

According to the present invention, the enteric-coated pellet for preparing the enteric-coated pellet tablet may be an enteric-coated pellet comprising a protective layer or an enteric-coated pellet comprising no protective layer.

According to the present invention, the tableting excipient may be conventional tableting excipients used in the art for tableting enteric-coated pellet tablets. In an embodiment according to the present invention, the tableting excipient includes a filler, a diluent, a disintegrant and a lubricant, wherein the filler and/or the diluent may be selected from, but is not limited to, one or more of starch, pregelatinized starch, lactose, mannitol and microcrystalline cellulose; the disintegrant may be selected from, but is not limited to, one or more of crospovidone, croscarmellose sodium and cross-linked sodium carboxymethyl starch; and the lubricant may be selected from, but is not limited to, one or more of talc, magnesium stearate, sodium stearyl fumarate and silica.

According to the present invention, the film coating may be conventional film coatings used in film coating of enteric-coated pellet tablets in the prior art. In an embodiment according to the present invention, the film coating comprises a coating powder, wherein the coating powder may be selected from, but is not limited to, one or more of hydroxypropylcellulose, polyvinylpyrrolidone, polyvinyl alcohol, methylcellulose, polyethylene glycol, talc, lakes and gastric soluble Opadry.

A tableting method for preparing an enteric-coated pellet tablet from the enteric-coated pellet according to the present invention, and optionally a method for coating with a film coating, are conventional methods for tableting and coating enteric-coated pellet tablets in the prior art.

According to a sixth aspect of the present invention, provided is an ilaprazole enteric-coated pellet capsule, comprising the above enteric-coated pellet having the protective layer according to the present invention.

According to the present invention, the capsule may be a conventional capsule used in the art for filling an enteric-coated pellet according to the required amount or specification; for example, the capsule may be a capsule shell that is sealed using a capsule sealing material, wherein the capsule shell material of the capsule may be selected from, but is not limited to, one or more of gelatin, starch, sodium alginate and hydroxypropyl methylcellulose; the capsule sealing material may be selected from, but is not limited to, one or more of gelatin, hydroxypropylmethylcellulose, methylcellulose, acrylic resin, β-cyclodextrin, ethylcellulose, modified starch, cellulose acetate, polyvinyl pyrrolidone (PVP), polyvinyl alcohol (PVA) and sodium carboxymethylcellulose.

The method for preparing an enteric-coated pellet tablet capsule from the enteric-coated pellet according to the present invention may be a conventional method for preparing the enteric-coated pellet capsule in the prior art.

According to a seventh aspect of the present invention, provided is an ilaprazole pellet dry suspension, comprising the enteric-coated pellet according to the present invention and dry suspension particles.

The method for preparing an enteric-coated pellet dry suspension from the enteric-coated pellet according to the present invention may be a conventional method for preparing the enteric-coated pellet dry suspension in the prior art.

In animal experimental studies that have been conducted, the inventors have found that a formulation comprising the enteric-coated pellet according to the present invention exhibits beneficial effects in the treatment and/or prevention of gastrointestinal diseases, wherein the gastrointestinal diseases mainly include heartburn, inflammatory bowel disease, Crohn's disease, irritable bowel syndrome, ulcerative colitis, peptic ulcer, stress ulcer, bleeding peptic ulcer, duodenal ulcer and duodenal ulcer recurrence, NSAID-associated gastric ulcer, adult active benign gastric ulcer, infectious enteritis, colitis, hyperacidity, dyspepsia, gastroparesis, zollinger-ellison syndrome, gastroesophageal reflux disease (GERD), *Helicobacter pylori*-associated disease or eradication of *Helicobacter pylori*, all grades of erosive esophagitis, short bowel syndrome, or any combination of the above diseases.

Thus, according to an eighth aspect of the present invention, provided is a method for treating and/or preventing gastrointestinal diseases, comprising a step of administering to a patient in need of such treatment and/or prevention a therapeutically and/or prophylactically effective amount of the enteric-coated pellet formulation according to the present invention. In an embodiment according to the present invention, the enteric-coated pellet formulation according to the present invention is the ilaprazole enteric-coated pellet tablet, the ilaprazole enteric-coated pellet capsule or the ilaprazole enteric-coated pellet dry suspension according to the present invention. The gastrointestinal diseases capable of being treated and/or prevented using this method include, but are not limited to, heartburn, inflammatory bowel disease, Crohn's disease, irritable bowel syndrome, ulcerative colitis, peptic ulcer, stress ulcer, bleeding peptic ulcer, duodenal ulcer and duodenal ulcer recurrence, NSAID-associated gastric ulcer, adult active gastric ulcer, infectious enteritis, colitis, hyperacidity, dyspepsia, gastroparesis, zollinger-ellison syndrome, gastroesophageal reflux disease (GERD), *Helicobacter pylori*-associated disease or eradication of *Helicobacter pylori*, all grades of erosive esophagitis, short bowel syndrome, or any combination of the above diseases.

Accordingly, according to a ninth aspect of the present invention, provided is use of the enteric-coated pellet and the formulation thereof according the present invention for preparing a medicament for treating and/or preventing gastrointestinal diseases, wherein the gastrointestinal diseases include, but are not limited to, heartburn, inflammatory bowel disease, Crohn's disease, irritable bowel syndrome, ulcerative colitis, peptic ulcer, stress ulcer, bleeding peptic ulcer, duodenal ulcer and duodenal ulcer recurrence, NSAID-associated gastric ulcer, adult active benign gastric ulcer, infectious enteritis, colitis, hyperacidity, dyspepsia, gastroparesis, zollinger-ellison syndrome, gastroesophageal reflux disease (GERD), *Helicobacter pylori*-associated disease or eradication of *Helicobacter pylori*, all grades of erosive esophagitis, short bowel syndrome, or any combination of the above diseases.

Furthermore, the enteric-coated pellet and the formulation thereof disclosed herein are used for preparing a medicament for treating and/or preventing gastrointestinal diseases, wherein the gastrointestinal diseases include, but are not limited to, duodenal ulcer and ulcer recurrence, gastric ulcer, gastroesophageal reflux disease (GERD), and *Helicobacter pylori*-associated diseases; or the medicament can be used for eradicating *Helicobacter pylori*, and also can be used for preventing peptic ulcer diseases caused by non-steroidal anti-inflammatory drugs, and gastrointestinal bleeding and associated ulcers caused by anti-platelet aggregation drugs (including but not limited to, clopidogrel, prasugrel and ticagrelor) and the like.

In the present invention, the inventors have found and eliminated influence factors which restrict the ilaprazole enteric-coated pellet and the formulation thereof to have both the good stability and the acid resistance (especially the acid resistance), and by the technical solutions of the present invention, the following beneficial effects have been achieved:

1) By providing at least two isolating layers (a first isolating layer and a second isolating layer and optionally other isolating layers) in the ilaprazole enteric-coated pellet and limiting the composition of these isolating layers (especially the first isolating layer and the second isolating layer), the enteric-coated pellet and the formulation thereof according to the present invention can have both better stability and acid resistance.
2) By adjusting the particle size of ilaprazole and/or the pharmaceutically acceptable salt thereof, the weight ratio of the water-insoluble alkaline compound and the binder in the first isolating layer, or the weight ratio of the water-insoluble inert substance capable of preventing the pellet from adhesion and the binder in the second isolating layer, or by additionally coating the protective layer, the enteric-coated pellet and the formulation thereof according to the present invention can have an increased dissolution rate of the active ingredients, thereby realizing improved bioavailability.
3) The ilaprazole enteric-coated pellet and the formulation thereof according to the present invention have a good in vivo acid inhibition effect in a human body, and can inhibit gastric acid to pH 4 or more within 1 h after being administrated, thereby achieving a clinical effect. The enteric-coated pellet tablet according to the present invention can achieve the effect quickly, thereby more quickly relieving the pain of patients.

DETAILED DESCRIPTION

Figure 1:
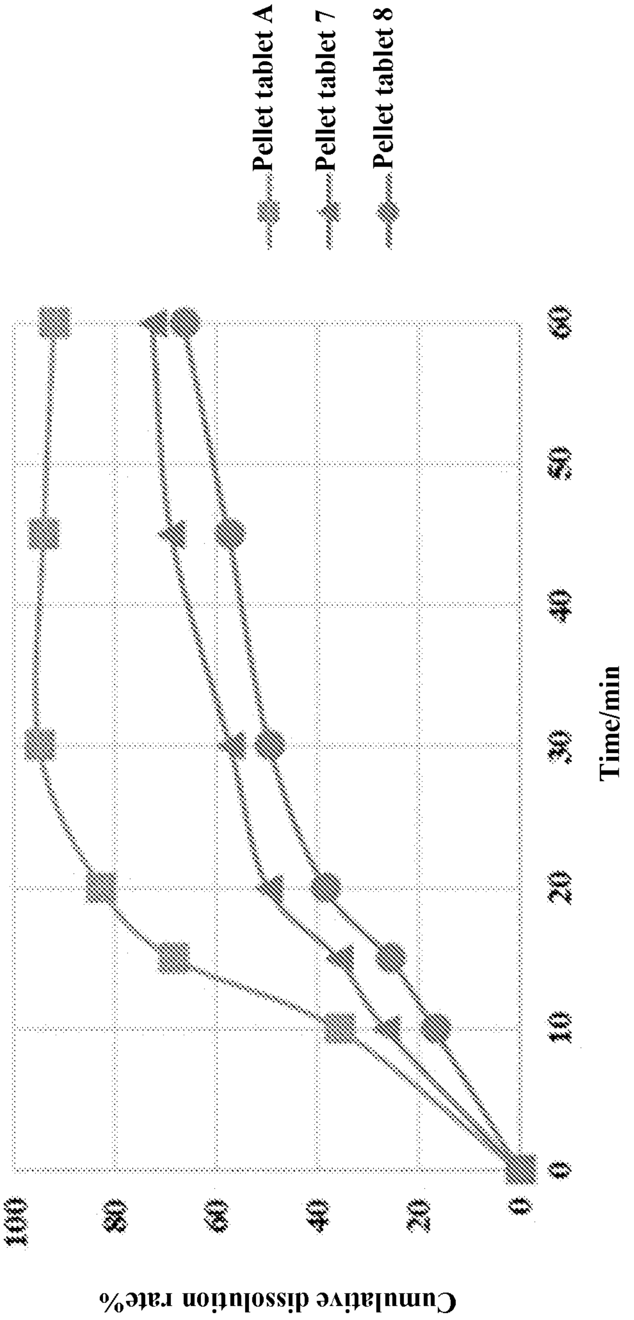
FIG. 1 is a graph of cumulative dissolution rates in an accelerated stability test of the pellet tablet according to the present invention versus comparative pellet tablets 7 and 8 (referred to as pellet tablets 7 and 8 in the figure) having different isolating layer formulas.

In this section, the enteric-coated pellet formulation according to the present invention and the method for preparing the same will be exemplified, mainly taking the ilaprazole enteric-coated pellet tablet and dry suspension according to the present invention as preferred examples.

The ilaprazole enteric-coated pellet tablet comprises pellets (which comprise a pellet core, a first isolating layer, a second isolating layer, an enteric coating layer and a protective layer in sequence from inside to outside), a tableting excipient and a film coating, wherein the pellet core comprises a blank pellet core and a drug-loading layer comprising ilaprazole and/or a pharmaceutically acceptable salt of ilaprazole (with a particle size D90 of preferably ≤50 μm), an alkaline compound, a surfactant and a binder; the first isolating layer comprises a water-insoluble alkaline compound and a binder, and does not comprise a water-soluble alkaline compound and a water-insoluble inert substance capable of preventing the pellets from adhesion; and the second isolating layer mainly comprises a binder and a water-insoluble inert substance (such as talc, silica, titanium dioxide and magnesium stearate, which can be used as an anti-adherent) capable of preventing the pellets from adhesion, but does not comprise an alkaline compound.

Preferably, the alkaline compound comprised in the pellet core is a water-insoluble alkaline compound; and more preferably, the water-insoluble alkaline compound comprised in the pellet core is the same as the water-insoluble alkaline compound comprised in the first isolating layer.

Specifically, the ilaprazole enteric-coated pellet tablet can comprise, but is not limited to, the following components and proportions: (in parts by weight) Ilaprazole enteric-coated pellet:

1) Pellet Core:

| | |
|---|---|
| Blank pellet core | 5-15; |
| Drug-loading layer, comprising: | |
| Ilaprazole (or a pharmaceutically acceptable salt thereof) | 5-15; |
| Alkaline compound | 5-15; |
| Surfactant | 0.2-0.6; |
| Binder | 8-24; |

2) First Isolating Layer:

| | |
|---|---|
| Binder | 5-36; |
| Water-insoluble alkaline compound | 5-36; |

3) Second Isolating Layer:

| | |
|---|---|
| Binder | 4-26; |
| Anti-adherent | 7-44; |

4) Enteric Coating Layer:

| | |
|---|---|
| Enteric coating material | 30-100 (solid content); |
| Anti-adherent | 1-5; |
| Plasticizer | 9-30; |

5) Protective Layer:

| | |
|---|---|
| Binder | 0.5-4; |
| Anti-adherent | 0.5-5; |
| Tableting | |

6) Tableting Excipient:

| | |
|---|---|
| Filler | 100-600; |
| Diluent | 50-200; |
| Disintegrant | 5-20; |
| Lubricant | 1-20; |

7) Film Coating:

| | |
|---|---|
| Coating powder | 10-40. |

The enteric-coated pellet tablet has high stability and acid resistance, and is suitable for ilaprazole with rather low stability. In addition, the ilaprazole enteric-coated pellet tablet also has good drug-loading rate and high dissolution rate/bioavailability.

The present invention will be further described below with reference to specific examples and drawings, which, however, are not intended to limit the present invention. The methods used in the following examples are conventional methods unless otherwise stated. The conclusions that can be shown by the test results in the following examples can be reasonably inferred based on the common knowledge in the art by those skilled in the art, and are not limited to the following text.

Example 1. Preparation of Enteric-Coated Pellets

In this example, taking ilaprazole and/or a pharmaceutically acceptable salt thereof as an example, the enteric-coated pellets A-G according to the present invention were prepared, and comparative pellets 3-18 were prepared for comparing the effects of different formulas of the component layers of the enteric-coated pellets on the properties of the enteric-coated pellets and their formulations. Compared to the enteric-coated pellets A-G according to the present invention, the comparative pellets 3 and 4 had different particle sizes of ilaprazole in the drug-loading layer; the comparative pellets 5-10 and 14-15 had different isolating layers; the comparative pellets 11, 16 and 17 had drug-loading layers with altered formulas; the comparative pellets 12-13 had different protective layers; and the comparative pellet 18 had an altered ratio of ilaprazole and/or a pharmaceutically acceptable salt thereof to the first excipient.

(I) Formula for Preparing the Component Layers of the Enteric-Coated Pellet 1.1 Formula and Method for Preparing Drug-Containing Pellet (W) and the Drug-Applying Rate of the Drug-Containing Pellet.

In this example, the drug-containing pellet (i.e., pellet core) comprising a blank pellet core and a drug-loading layer was prepared.

1) Formula W1 of the Drug-Containing Pellet (Unit: g)

| | |
|---|---|
| Ilaprazole (particle size D90: 46.8 μm) | 100 |
| Sucrose pellet core (particle size: 250-350 μm) | 100 |
| Magnesium hydroxide | 100 |
| Polysorbate-80 | 4 |
| Hydroxypropylcellulose-SSL | 150 |
| Purified water | 3000 |

Preparation Process:

150 g of hydroxypropylcellulose-SSL and 4 g of polysorbate-80 were weighed and dissolved in 3000 g of purified water to obtain a hydroxypropylcellulose binder solution, and 100 g of magnesium hydroxide was added to the binder solution and dispersed for 5 min at a high shear rate of 10,000 rpm; and 100 g of ilaprazole starting material with a particle size D90 of 46.8 m was dispersed into the magnesium hydroxide-containing binder and uniformly dispersed at a high shear rate of 10,000 rpm, and then the ilaprazole suspension was sprayed onto the sucrose pellet core through a GLATT GPCG-1 fluidized bed.

The specific process parameters were as follows:

| Parameters | Preheating | Drug applying | Drying |
|---|---|---|---|
| Inlet air volume ($m^3$/min) | 45 | 50-80 | 60 |
| Inlet air temperature (° C.) | 40-50 | 40-50 | 40-50 |
| Material temperature (° C.) | 38-40 | 35-40 | 35-40 |
| Atomizing pressure (bar) | 0.1 | 0.1-0.2 | 0.1 |
| Spraying rate (g/min) | | 0.5-4 | |

The drug-applying rate $W_1$ of the drug-containing pellet=(actual content of drug-containing pellet)/(theoretical content of drug-containing pellet)×100%=95.6%

2) Formula W2 of the Drug-Containing Pellet (Unit: g)

| | |
|---|---|
| Ilaprazole magnesium (particle size D90≤: 50 μm) | 50 |
| Microcrystalline cellulose pellet core | 50 |
| Hydroxypropylcellulose-SSL | 100 |
| Sodium dodecyl sulfate | 2 |
| Magnesium carbonate | 150 |
| Purified water | 2000 |

Preparation Process:

100 g of hydroxypropylcellulose-SSL and 2 g of sodium dodecyl sulfate according to the formula were weighed and dissolved in 2000 g of purified water, and 150 g of magnesium carbonate was added and dispersed for 5 min at a high shear rate of 10,000 rpm; and 50 g of ilaprazole magnesium was dispersed into the magnesium carbonate-containing binder and uniformly dispersed at a high shear rate of 10,000 rpm, and then the ilaprazole magnesium suspension was sprayed onto the microcrystalline cellulose pellet core through a GLATT GPCG-1 fluidized bed.

The specific process parameters were as follows:

| Parameters | Preheating | Drug applying | Drying |
|---|---|---|---|
| Inlet air volume ($m^3$/min) | 35 | 40-60 | 50 |
| Inlet air temperature (° C.) | 40-50 | 40-50 | 40-50 |
| Material temperature (° C.) | 38-40 | 35-40 | 35-40 |
| Atomizing pressure (bar) | 0.1 | 0.1-0.2 | 0.1 |
| Spraying rate (g/min) | | 0.5-3 | |

The drug-applying rate $W_2$ of the drug-containing pellet=(actual content of drug-containing pellet)/(theoretical content of drug-containing pellet)×100%=91.4%

3) Formula W3 of the Drug-Containing Pellet (Unit: g)

| | |
|---|---|
| Ilaprazole zinc (particle size D90 ≤ 50 μm) | 150 |
| Sucrose pellet core | 150 |
| Polyvinylpyrrolidone K30 | 240 |
| Sodium dodecyl sulfate | 6 |
| Calcium carbonate | 150 |
| Purified water | 4800 |

Preparation Process:

240 g of polyvinylpyrrolidone K30 and 6 g of sodium dodecyl sulfate according to the formula were weighed and dissolved in 4800 g of purified water, and 150 g of calcium carbonate was added and uniformly dispersed at a high shear rate of 10,000 rpm; and 150 g of ilaprazole zinc was dispersed into the calcium carbonate-containing binder and uniformly dispersed at a high shear rate of 10,000 rpm, and then the ilaprazole zinc suspension was sprayed onto the sucrose pellet core through a GLATT GPCG-1 fluidized bed.

The specific process parameters were as follows:

| Parameters | Preheating | Drug applying | Drying |
|---|---|---|---|
| Inlet air volume ($m^3$/min) | 45 | 60-80 | 60 |
| Inlet air temperature (° C.) | 40-50 | 45-55 | 45-55 |
| Material temperature (° C.) | 38-40 | 35-40 | 35-40 |
| Atomizing pressure (bar) | 0.1 | 0.1-0.2 | 0.1 |
| Spraying rate (g/min) | | 0.5-3 | |

The drug-applying rate $W_3$ of the drug-containing pellet=(actual content of drug-containing pellet)/(theoretical content of drug-containing pellet)×100%=92.4%

4) Formula W4 of the Drug-Containing Pellet (Unit: g)

| | |
|---|---|
| Ilaprazole (particle size D90 ≤ 50 μm) | 150 |
| Mannitol pellet core | 100 |
| Polyvinylpyrrolidone K30 | 180 |
| Polysorbate-80 | 6 |
| Magnesium oxide | 50 |
| Purified water | 3000 |

Preparation Process:

180 g of polyvinylpyrrolidone K30 and 6 g of polysorbate-80 according to the formula were weighed and dissolved in 3000 g of purified water, and 50 g of magnesium oxide was added and uniformly dispersed at a high shear rate at 10,000 rpm; and 150 g of ilaprazole was dispersed into the magnesium oxide-containing binder and uniformly dispersed at a high shear rate of 10,000 rpm, and then the ilaprazole suspension was sprayed onto the mannitol pellet core through a GLATT GPCG-1 fluidized bed.

The specific process parameters were as follows:

| Parameters | Preheating | Drug applying | Drying |
|---|---|---|---|
| Inlet air volume ($m^3$/min) | 50 | 50-70 | 60 |
| Inlet air temperature (° C.) | 40-50 | 45-55 | 45-55 |
| Material temperature (° C.) | 38-40 | 35-40 | 35-40 |
| Atomizing pressure (bar) | 0.1 | 0.1-0.2 | 0.1 |
| Spraying rate (g/min) | | 0.5-4 | |

The drug-applying rate $W_4$ of the drug-containing pellet=(actual content of drug-containing pellet)/(theoretical content of drug-containing pellet)×100%=93.300

| | |
|---|---|
| 5) Formula W5 of the drug-containing pellet (unit: g) | 150 |
| Ilaprazole (particle size D90 ≤ 50 μm) | |
| Sucrose pellet core | 150 |
| Hydroxypropyl methylcellulose-E5 | 80 |
| Polysorbate-80 | 6 |
| Magnesium hydroxide | 50 |
| Purified water | 1600 |

Preparation Process:

80 g of hydroxypropyl methylcellulose-E5 and 6 g of polysorbate-80 according to the formula were weighed and dissolved in 1600 g of purified water, and 50 g of magnesium hydroxide was added and uniformly dispersed at a high shear rate at 10,000 rpm; and 150 g of ilaprazole was dispersed into the magnesium hydroxide-containing binder and uniformly dispersed at a high shear rate of 10,000 rpm, and then the ilaprazole suspension was sprayed onto the sucrose pellet core through a GLATT GPCG-1 fluidized bed.

The specific process parameters were as follows:

| Parameters | Preheating | Drug applying | Drying |
|---|---|---|---|
| Inlet air volume ($m^3$/min) | 50 | 50-70 | 60 |
| Inlet air temperature (° C.) | 40-50 | 45-55 | 45-55 |
| Material temperature (° C.) | 38-40 | 35-40 | 35-40 |
| Atomizing pressure (bar) | 0.1 | 0.1-0.2 | 0.1 |
| Spraying rate (g/min) | | 0.5-4 | |

The drug-applying rate $W_5$ of the drug-containing pellet=(actual content of drug-containing pellet)/(theoretical content of drug-containing pellet)×100%=94.1%

6) Formula W6 of the Drug-Containing Pellet (Unit: g)

| | |
|---|---|
| Ilaprazole (particle size D90 ≤ 50 μm) | 100 |
| Sucrose pellet core (250-350 μm) | 100 |
| Hydroxypropylcellulose-SSL | 100 |
| Purified water | 3000 |

Preparation Process:

100 g of hydroxypropylcellulose-SSL according to the formula was weighed and dissolved in 3000 g of purified water to obtain a hydroxypropylcellulose binder solution, and 100 g of ilaprazole starting material was dispersed into the binder solution and uniformly dispersed at a high shear rate 10,000 rpm, and then the ilaprazole suspension was sprayed onto the sucrose pellet core through a GLATT GPCG-1 fluidized bed.

The specific process parameters were as follows:

| Parameters | Preheating | Drug applying | Drying |
|---|---|---|---|
| Inlet air volume ($m^3$/min) | 45 | 50-80 | 60 |
| Inlet air temperature (° C.) | 40-50 | 40-50 | 40-50 |
| Material temperature (° C.) | 38-40 | 35-40 | 35-40 |
| Atomizing pressure (bar) | 0.1 | 0.1-0.2 | 0.1 |
| Spraying rate (g/min) | | 0.5-4 | |

The drug-applying rate $W_6$ of the drug-containing pellet=(actual content of drug-containing pellet)/(theoretical content of drug-containing pellet)×100%=93.4%

7) Formula W7 of the Drug-Containing Pellet (Unit: g)

| | |
|---|---|
| Ilaprazole (particle size D90 ≤ 50 μm) | 100 |
| Sucrose pellet core (250-350 μm) | 100 |
| Magnesium hydroxide | 100 |
| Hydroxypropylcellulose-SSL | 100 |
| Purified water | 3000 |

Preparation Process:

100 g of hydroxypropylcellulose-SSL according to the formula was weighed and dissolved in 3000 g of purified water to obtain a hydroxypropylcellulose binder solution, and 100 g of ilaprazole starting material and 100 g of magnesium hydroxide were dispersed into the binder solution and uniformly dispersed at a high shear rate 10,000 rpm, and then the ilaprazole suspension was sprayed onto the sucrose pellet core through a GLATT GPCG-1 fluidized bed.

The specific process parameters were as follows:

| Parameters | Preheating | Drug applying | Drying |
|---|---|---|---|
| Inlet air volume ($m^3$/min) | 45 | 50-80 | 60 |
| Inlet air temperature (° C.) | 40-50 | 40-50 | 40-50 |
| Material temperature (° C.) | 38-40 | 35-40 | 35-40 |
| Atomizing pressure (bar) | 0.1 | 0.1-0.2 | 0.1 |
| Spraying rate (g/min) | | 0.5-4 | |

The drug-applying rate $W_7$ of the drug-containing pellet=(actual content of drug-containing pellet)/(theoretical content of drug-containing pellet)×100%=95.4%

8) Formula W8 of the Drug-Containing Pellet

This formula was the same as the formula W1 of the drug-containing pellet, except that the particle size D90 of ilaprazole was greater than or equal to 80 m and less than or equal to 100 m. The drug-applying rate $W_8$ of the drug-containing pellet=(actual content of drug-containing pellet)/(theoretical content of drug-containing pellet)×100%=87.2%

9) Formula W9 of the Drug-Containing Pellet

This formula was the same as the formula W1 of drug-containing pellet, except that the particle size D90 of ilaprazole was >100 m. The drug-applying rate W9 of the drug-containing pellet=(actual content of drug-containing pellet)/(theoretical content of drug-containing pellet)×100%=79.3%

10) Formula W10 of the Drug-Containing Pellet (Unit: g)

| | |
|---|---|
| Ilaprazole (particle size D90: 46.8 μm) | 100 |
| Sucrose pellet core (particle size: 250-350 μm) | 100 |
| Polysorbate-80 | 4 |
| Hydroxypropylcellulose-SSL | 150 |
| Purified water | 3000 |

Preparation Process:

150 g of hydroxypropylcellulose-SSL and 4 g of polysorbate-80 were weighed and dissolved in 3000 g of purified water to obtain a hydroxypropylcellulose binder solution, and 100 g of ilaprazole starting material with a particle size D90 of 46.8 m was dispersed into the polysorbate-80-containing binder and uniformly dispersed at a high shear rate of 10,000 rpm, and then the ilaprazole suspension was sprayed onto the sucrose pellet core through a GLATT GPCG-1 fluidized bed.

The specific process parameters were as follows:

| Parameters | Preheating | Drug applying | Drying |
|---|---|---|---|
| Inlet air volume ($m^3$/min) | 45 | 50-80 | 60 |
| Inlet air temperature (° C.) | 40-50 | 40-50 | 40-50 |
| Material temperature (° C.) | 38-40 | 35-40 | 35-40 |
| Atomizing pressure (bar) | 0.1 | 0.1-0.2 | 0.1 |
| Spraying rate (g/min) | | 0.5-4 | |

The drug-applying rate $W_{10}$ of the drug-containing pellet=(actual content of drug-containing pellet)/(theoretical content of drug-containing pellet)×100%=97.6%

11) Formula W11 of the drug-containing pellet (unit: g)

| | |
|---|---|
| Ilaprazole magnesium (particle size D90 ≤ 50 μm) | 50 |
| Microcrystalline cellulose pellet core | 50 |
| Hydroxypropylcellulose-SSL | 100 |
| Sodium dodecyl sulfate | 2 |
| Magnesium carbonate | 200 |
| Purified water | 2000 |

Preparation Process:

100 g of hydroxypropylcellulose-SSL and 2 g of sodium dodecyl sulfate according to the formula were weighed and dissolved in 2000 g of purified water, and 200 g of magnesium carbonate was added and dispersed for 5 min at a high shear rate of 10,000 rpm; and 50 g of ilaprazole magnesium was dispersed into the magnesium carbonate-containing binder and uniformly dispersed at a high shear rate of 10,000 rpm, and then the magnesium ilaprazole suspension was sprayed onto the microcrystalline cellulose pellet core through a GLATT GPCG-1 fluidized bed.

The specific process parameters were as follows:

| Parameters | Preheating | Drug applying | Drying |
|---|---|---|---|
| Inlet air volume ($m^3$/min) | 35 | 40-60 | 50 |
| Inlet air temperature (° C.) | 40-50 | 40-50 | 40-50 |
| Material temperature (° C.) | 38-40 | 35-40 | 35-40 |
| Atomizing pressure (bar) | 0.1 | 0.1-0.2 | 0.1 |
| Spraying rate (g/min) | | 0.5-3 | |

The drug-applying rate $W_{11}$ of the drug-containing pellet=(actual content of drug-containing pellet)/(theoretical content of drug-containing pellet)×100%=92.5%

12) Formula W12 of the Drug-Containing Pellet (Unit: g)

| | |
|---|---|
| Ilaprazole (particle size D90 ≤ 50 μm) | 200 |
| Sucrose pellet core | 150 |
| Hydroxypropyl methylcellulose-E5 | 100 |
| Polysorbate-80 | 6 |
| Magnesium hydroxide | 50 |
| Purified water | 2000 |

Preparation Process:

100 g of hydroxypropyl methylcellulose-E5 and 6 g of polysorbate-80 according to the formula were weighed and dissolved in 2000 g of purified water, and 50 g of magnesium hydroxide was added and uniformly dispersed at a high shear rate at 10,000 rpm; and 200 g of ilaprazole was dispersed into the magnesium hydroxide-containing binder and uniformly dispersed at a high shear rate of 10,000 rpm, and then the ilaprazole suspension was sprayed onto the sucrose pellet core through a GLATT GPCG-1 fluidized bed.

The specific process parameters were as follows:

| Parameters | Preheating | Drug applying | Drying |
|---|---|---|---|
| Inlet air volume ($m^3$/min) | 50 | 50-70 | 60 |
| Inlet air temperature (° C.) | 40-50 | 45-55 | 45-55 |
| Material temperature (° C.) | 38-40 | 35-40 | 35-40 |
| Atomizing pressure (bar) | 0.1 | 0.1-0.2 | 0.1 |
| Spraying rate (g/min) | | 0.5-4 | |

The drug-applying rate $W_{12}$ of the drug-containing pellet=(actual content of drug-containing pellet)/(theoretical content of drug-containing pellet)×100%=93.8%

13) Formula W13 of the Drug-Containing Pellet (Unit: g)

| | |
|---|---|
| Ilaprazole (particle size D90 ≤50 μm) | 180 |
| Microcrystalline cellulose pellet core | 50 |
| Hydroxypropylcellulose-SSL | 100 |
| Sodium dodecyl sulfate | 2 |
| Magnesium carbonate | 30 |
| Purified water | 2000 |

Preparation Process:

100 g of hydroxypropylcellulose-SSL and 2 g of sodium dodecyl sulfate according to the formula were weighed and dissolved in 2000 g of purified water, and 30 g of magnesium carbonate was added and dispersed for 5 min at a high shear rate of 10,000 rpm; and 180 g of ilaprazole was dispersed into the magnesium carbonate-containing binder and uniformly dispersed at a high shear rate of 10,000 rpm, and then the ilaprazole suspension was sprayed onto the microcrystalline cellulose pellet core through a GLATT GPCG-1 fluidized bed.

The specific process parameters were as follows:

| Parameters | Preheating | Drug applying | Drying |
|---|---|---|---|
| Inlet air volume ($m^3$/min) | 35 | 40-60 | 50 |
| Inlet air temperature (° C.) | 40-50 | 40-50 | 40-50 |
| Material temperature (° C.) | 38-40 | 35-40 | 35-40 |
| Atomizing pressure (bar) | 0.1 | 0.1-0.2 | 0.1 |
| Spraying rate (g/min) | | 0.5-3 | |

The drug-applying rate $W_{13}$ of the drug-containing pellet=(actual content of drug-containing pellet)/(theoretical content of drug-containing pellet)×100%=94.5%

1.2 Formula for Preparing the Isolating Layer (G)

1) Formula G1 of the Isolating Layer (Unit: g)

| | |
|---|---|
| Ilaprazole-containing pellet | 90 |
| Formula of the first isolating layer | |
| Hydroxypropylcellulose-SSL | 10 |
| Magnesium carbonate | 10 |
| Purified water | 200 |
| Formula of the second isolating layer | |
| Hydroxypropylcellulose-SSL | 8 |
| Talc | 14 |
| Purified water | 160 |

Preparation Process:

10 g of hydroxypropylcellulose-SSL according to the formula was weighed and dissolved in 200 g of purified water, and then 10 g of magnesium carbonate was added and uniformly dispersed at a high shear rate of 10,000 rpm to obtain a coating suspension of the first isolating layer. 8 g of hydroxypropylcellulose-SSL was weighed and dissolved in 160 g of purified water, and 14 g of talc was added and uniformly dispersed at a high shear rate of 10,000 rpm to obtain a coating suspension of the second isolating layer. The coating suspensions of the two isolating layers were sprayed onto the drug-containing pellet core sequentially through a GLATT GPCG-1 fluidized bed.

The specific process parameters were as follows:

| Parameters | Preheating | Isolating coating | Drying |
|---|---|---|---|
| Inlet air volume ($m^3$/min) | 50 | 50-60 | 60 |
| Inlet air temperature (° C.) | 40-50 | 45-55 | 45-55 |
| Material temperature (° C.) | 38-40 | 35-40 | 35-40 |
| Atomizing pressure (bar) | 0.1 | 0.1-0.2 | 0.1 |
| Spraying rate (g/min) | | 0.5-3.5 | |

2) Formula G2 of the Isolating Layer (Unit: g)

| | |
|---|---|
| Ilaprazole-containing pellet | 90 |
| Formula of the first isolating layer | |
| Hydroxypropylcellulose-SSL | 23 |
| Magnesium carbonate | 23 |
| Purified water | 460 |
| Formula of the second isolating layer | |
| Hydroxypropylcellulose-SSL | 17.2 |
| Talc | 28.8 |
| Purified water | 344 |

Preparation Process:

23 g of hydroxypropylcellulose-SSL according to the formula was weighed and dissolved in 460 g of purified water, and then 23 g of magnesium carbonate was added and uniformly dispersed at a high shear rate of 10,000 rpm to obtain a coating suspension of the first isolating layer. 17.2 g of hydroxypropylcellulose-SSL was weighed and dissolved in 344 g of purified water, and 28.8 g of talc was added and uniformly dispersed at a high shear rate of 10,000 rpm to obtain a coating suspension of the second isolating layer. The coating suspensions of the two isolating layers were sprayed onto the drug-containing pellet core sequentially through a GLATT GPCG-1 fluidized bed.

The formula G1 of the isolating layer was referred to for specific process parameters.

3) Formula G3 of the Isolating Layer (for Comparative Pellet 7) (Unit: g)

| | |
|---|---|
| Ilaprazole-containing pellet | 90 |
| Formula of the first isolating layer | |
| Hydroxypropylcellulose-SSL | 88 |
| Magnesium carbonate | 88 |
| Purified water | 1140 |
| Formula of the second isolating layer | |
| Hydroxypropylcellulose-SSL | 17.2 |
| Talc | 28.8 |
| Purified water | 520 |

Preparation Process:

88 g of hydroxypropylcellulose-SSL according to the formula was weighed and dissolved in 1140 g of purified water, and then 88 g of magnesium carbonate was added and uniformly dispersed at a high shear rate of 10,000 rpm to obtain a coating suspension of the first isolating layer. 17.2 g of hydroxypropylcellulose-SSL was weighed and dissolved in 520 g of purified water, and 28.8 g of talc was added and uniformly dispersed at a high shear rate of 10,000 rpm to obtain a coating suspension of the second isolating layer. The coating suspensions of the two isolating layers were sprayed onto the drug-containing pellet core sequentially through a GLATT GPCG-1 fluidized bed.

The formula G1 of the isolating layer was referred to for specific process parameters.

4) Formula G4 of the Isolating Layer (for Comparative Pellet 9) (Unit: g)

| | |
|---|---|
| Ilaprazole-containing pellet | 90 |
| Formula of the first isolating layer | |
| Hydroxypropylcellulose-SSL | 23 |
| Magnesium carbonate | 23 |
| Talc | 11.5 |
| Purified water | 460 |
| Formula of the second isolating layer | |
| Hydroxypropylcellulose-SSL | 17.2 |
| Talc | 28.8 |
| Purified water | 344 |

Preparation Process:

23 g of hydroxypropylcellulose-SSL according to the formula was weighed and dissolved in 460 g of purified water, and then 23 g of magnesium carbonate and 11.5 g of talc were added and uniformly dispersed at a high shear rate of 10,000 rpm to obtain a coating suspension of the first isolating layer. 17.2 g of hydroxypropylcellulose-SSL was weighed and dissolved in 344 g of purified water, and 28.8 g of talc was added and uniformly dispersed at a high shear rate of 10,000 rpm to obtain a coating suspension of the second isolating layer. The coating suspensions of the two isolating layers were sprayed onto the drug-containing pellet core sequentially through a GLATT GPCG-1 fluidized bed.

The formula G1 of the isolating layer was referred to for specific process parameters.

5) Formula G5 of the Isolating Layer (for Comparative Pellet 10) (Unit: g)

| | |
|---|---|
| Ilaprazole-containing pellet | 90 |
| Formula of the first isolating layer | |
| Hydroxypropylcellulose-SSL | 23 |
| Sodium carbonate | 23 |
| Purified water | 460 |
| Formula of the second isolating layer | |
| Hydroxypropylcellulose-SSL | 17.2 |
| Talc | 28.8 |
| Purified water | 344 |

Preparation Process:

23 g of hydroxypropylcellulose-SSL according to the formula was weighed and dissolved in 460 g of purified water, and then 23 g of sodium carbonate was added and uniformly dispersed at a high shear rate of 10,000 rpm to obtain a coating suspension of the first isolating layer. 17.2 g of hydroxypropylcellulose-SSL was weighed and dissolved in 344 g of purified water, and 28.8 g of talc was added and uniformly dispersed at a high shear rate of 10,000 rpm to obtain a coating suspension of the second isolating layer. The coating suspensions of the two isolating layers were sprayed onto the drug-containing pellet core sequentially through a GLATT GPCG-1 fluidized bed.

The formula G1 of the isolating layer was referred to for specific process parameters.

6) Formula G6 of the Isolating Layer (for Comparative Pellet 5) (Unit: g)

| | |
|---|---|
| Ilaprazole-containing pellet | 90 |
| Hydroxypropylcellulose-SSL | 33 |
| Talc | 57 |
| Purified water | 890 |

Preparation Process:

33 g of hydroxypropylcellulose-SSL according to the formula was weighed and dissolved in 890 g of purified water, and then 57 g of talc was added and uniformly dispersed at a high shear rate of 10,000 rpm to obtain a coating suspension of the isolating layer. The coating suspension of the isolating layer was sprayed onto the drug-containing pellet core through a GLATT GPCG-1 fluidized bed.

The formula G1 of the isolating layer was referred to for specific process parameters.

7) Formula G7 of the Isolating Layer (for Comparative Pellet 6) (Unit: g)

| | |
|---|---|
| Ilaprazole-containing pellet | 90 |
| Formula of the first isolating layer | |
| Povidone K30 | 23 |
| Titanium dioxide | 23 |
| Purified water | 460 |
| Formula of the second isolating layer | |
| Povidone K30 | 26 |
| Silica | 44 |
| Purified water | 520 |

Preparation Process:

23 g of povidone K30 according to the formula was weighed and dissolved in 460 g of purified water, and then 23 g of titanium dioxide was added and uniformly dispersed at a high shear rate of 10,000 rpm to obtain a coating suspension of the first isolating layer. 26 g of povidone K30 was weighed and dissolved in 520 g of purified water, and then 44 g of silica was added and uniformly dispersed at a high shear rate of 10,000 rpm to obtain a coating suspension of the second isolating layer; the coating suspensions of the two isolating layers were sprayed onto the drug-containing pellet core sequentially through a GLATT GPCG-1 fluidized bed.

The formula G1 of the isolating layer was referred to for specific process parameters.

8) Formula G8 of the Isolating Layer (for Comparative Pellet 8) (Unit: g)

| | |
|---|---|
| Ilaprazole-containing pellet | 90 |
| Formula of the first isolating layer | |
| Hydroxypropylcellulose-SSL | 23 |
| Magnesium carbonate | 23 |
| Purified water | 720 |
| Formula of the second isolating layer | |
| Hydroxypropylcellulose-SSL | 52 |
| Talc | 100 |
| Purified water | 1040 |

Preparation Process:

23 g of hydroxypropylcellulose-SSL according to the formula was weighed and dissolved in 720 g of purified water, and then 23 g of magnesium carbonate was added and uniformly dispersed at a high shear rate of 10,000 rpm to obtain a coating suspension of the first isolating layer. 52 g of hydroxypropylcellulose-SSL was weighed and dissolved in 1040 g of purified water, and 100 g of talc was added and uniformly dispersed at a high shear rate of 10,000 rpm to obtain a coating suspension of the second isolating layer. The coating suspensions of the two isolating layers were sprayed onto the drug-containing pellet core sequentially through a GLATT GPCG-1 fluidized bed.

The formula G1 of the isolating layer was referred to for specific process parameters.

9) Formula G9 of the Isolating Layer (for Comparative Pellet 14) (Unit: g)

| | |
|---|---|
| Ilaprazole-containing pellet | 90 |
| Formula of the first isolating layer | |
| Hydroxypropylcellulose-SSL | 10 |
| Sodium carbonate | 5 |
| Talc | 5 |
| Purified water | 200 |
| Formula of the second isolating layer | |
| Hydroxypropylcellulose-SSL | 8 |
| Talc | 14 |
| Purified water | 160 |

Preparation Process:

10 g of hydroxypropylcellulose-SSL, 5 g of sodium carbonate and 5 g of talc according to the formula were weighed and dissolved in 200 g of purified water to obtain a coating suspension of the first isolating layer. 8 g of hydroxypropylcellulose-SSL was weighed and dissolved in 160 g of purified water, and 14 g of talc was added and uniformly dispersed at a high shear rate of 10,000 rpm to obtain a coating suspension of the second isolating layer. The coating suspensions of the two isolating layers were sprayed onto the drug-containing pellet core sequentially through a GLATT GPCG-1 fluidized bed.

The formula G1 of the isolating layer was referred to for specific process parameters.

10) Formula G10 of the Isolating Layer (Unit: g)

| | |
|---|---|
| Ilaprazole-containing pellet | 90 |
| Formula of the first isolating layer | |
| Hydroxypropyl methylcellulose-E5 | 15 |
| Magnesium oxide | 15 |
| Purified water | 300 |
| Formula of the second isolating layer | |
| Hydroxypropyl methylcellulose-E5 | 12 |
| Titanium dioxide | 21 |
| Purified water | 240 |

Preparation Process:

15 g of hydroxypropyl methylcellulose-E5 according to the formula was weighed and dissolved in 300 g of purified water, and then 15 g of magnesium oxide was added and uniformly dispersed at a high shear rate of 10,000 rpm to obtain a coating suspension of the first isolating layer. 12 g of hydroxypropyl methylcellulose-E5 was weighed and dissolved in 240 g of purified water, and 21 g of titanium dioxide was added and uniformly dispersed at a high shear rate of 10,000 rpm to obtain a coating suspension of the second isolating layer. The coating suspensions of the two isolating layers were sprayed onto the drug-containing pellet core sequentially through a GLATT GPCG-1 fluidized bed.

The formula G1 of the isolating layer was referred to for specific process parameters.

11) Formula G11 of the Isolating Layer (Unit: g)

| | |
|---|---|
| Ilaprazole-containing pellet | 90 |
| Formula of the first isolating layer | |
| Hydroxypropylcellulose-SSL | 20 |
| Magnesium hydroxide | 20 |
| Purified water | 400 |
| Formula of the second isolating layer | |
| Hydroxypropylcellulose-SSL | 8 |
| Talc | 14 |
| Purified water | 160 |

Preparation Process:

20 g of hydroxypropylcellulose-SSL according to the formula was weighed and dissolved in 400 g of purified water, and then 20 g of magnesium hydroxide was added and uniformly dispersed at a high shear rate of 10,000 rpm to obtain a coating suspension of the first isolating layer. 8 g of hydroxypropylcellulose-SSL was weighed and dissolved in 160 g of purified water, and 14 g of talc was added and uniformly dispersed at a high shear rate of 10,000 rpm to obtain a coating suspension of the second isolating layer. The coating suspensions of the two isolating layers were sprayed onto the drug-containing pellet core sequentially through a GLATT GPCG-1 fluidized bed.

The formula G1 of the isolating layer was referred to for specific process parameters.

12) Formula G12 of the Isolating Layer (Unit: g)

| | |
|---|---|
| Ilaprazole-containing pellet | 90 |
| Formula of the first isolating layer | |
| Hydroxypropylcellulose-SSL | 23 |
| Magnesium hydroxide | 23 |
| Purified water | 460 |
| Formula of the second isolating layer | |
| Hydroxypropylcellulose-SSL | 46 |
| Purified water | 920 |

Preparation Process:

23 g of hydroxypropylcellulose-SSL according to the formula was weighed and dissolved in 460 g of purified water, and then 23 g of magnesium hydroxide was added and uniformly dispersed at a high shear rate of 10,000 rpm to obtain a coating suspension of the first isolating layer. 46 g of hydroxypropylcellulose-SSL was weighed and dissolved in 920 g of purified water to obtain a coating suspension of the second isolating layer. The coating suspensions of the two isolating layers were sprayed onto the drug-containing pellet core sequentially through a GLATT GPCG-1 fluidized bed.

The formula G1 of the isolating layer was referred to for specific process parameters.

1.3 Formula for Preparing the Enteric Coating Layer (C)

Formula C1 of the Enteric Coating Layer (Unit: g)

| | |
|---|---|
| Ilaprazole isolated pellet | 92 |
| Eudragit L30D-55 | 223.8 |
| Talc | 3.4 |
| Triethyl citrate | 20.1 |
| Purified water | 447.6 |

Preparation Process:

20.1 g of triethyl citrate according to the formula was weighed and dissolved in 447.6 g of purified water, and 3.4 g of talc was uniformly dispersed at a high shear rate of 10,000 rpm; 223.8 g of Eudragit L30D-55 was added and the mixture was stirred for 45 min to obtain an enteric coating solution for later use; and the enteric coating solution was sprayed onto the isolated pellet through a GLATT GPCG-1 fluidized bed.

The specific process parameters were as follows:

| Parameters | Preheating | Enteric coating | Drying |
|---|---|---|---|
| Inlet air volume (m3/min) | 50 | 50-80 | 60 |
| Inlet air temperature (° C.) | 35-30 | 33-42 | 35-45 |
| Material temperature (° C.) | 25-30 | 25-30 | 30-35 |
| Atomizing pressure (bar) | 0.1 | 0.15-0.25 | 0.1 |
| Spraying rate (g/min) | | 0.5-3 | |

1.4 Preparation of the Protective Layer (B)

1) Formula B1 of the Protective Layer (Unit: g)

| | |
|---|---|
| Ilaprazole enteric-coated pellet | 100 |
| Hydroxypropyl methylcellulose-E5 | 2.5 |
| Magnesium stearate | 1.2 |
| Purified water | 50 |

Preparation Process:

2.5 g of hydroxypropyl methylcellulose-E5 according to the formula was weighed and dissolved in 50 g of purified water, and then 1.2 g of magnesium stearate was added and uniformly dispersed at a high shear rate of 5000 rpm to obtain a coating solution of the protective layer. The coating solution of the protective layer was sprayed onto the enteric-coated pellet through a GLATT GPCG-1 fluidized bed.

The specific process parameters were as follows:

| Parameters | Preheating | Isolating coating | Drying |
|---|---|---|---|
| Inlet air volume ($m^3$/min) | 50 | 50-60 | 60 |
| Inlet air temperature (° C.) | 40-50 | 45-55 | 45-55 |
| Material temperature (° C.) | 38-40 | 35-40 | 35-40 |
| Atomizing pressure (bar) | 0.1 | 0.1-0.2 | 0.1 |
| Spraying rate (g/min) | | 0.5-3.5 | |

2) Formula B2 of the Protective Layer (Unit: g)

| | |
|---|---|
| Ilaprazole enteric-coated pellet | 100 |
| Hydroxypropylcellulose-SSL | 0.5 |
| Magnesium stearate | 0.5 |
| Purified water | 10 |

Preparation Process:

0.5 g of hydroxypropylcellulose-SSL according to the formula was weighed and dissolved in 10 g of purified water, and then 0.5 g of magnesium stearate was added and uniformly dispersed at a high shear rate of 3000 rpm to obtain a coating solution of the protective layer. The coating solution of the protective layer was sprayed onto the enteric-coated pellet through a GLATT GPCG-1 fluidized bed.

The formula B1 of the protective layer was referred to for specific process parameters.

3) Formula B3 of the Protective Layer (Unit: g)

| | |
|---|---|
| Ilaprazole enteric-coated pellet | 100 |
| Hydroxypropylcellulose-SSL | 4 |
| Magnesium stearate | 5 |
| Purified water | 80 |

Preparation Process:

4 g of hydroxypropylcellulose-SSL according to the formula was weighed and dissolved in 80 g of purified water, and then 5 g of magnesium stearate was added and uniformly dispersed at a high shear rate of 5000 rpm to obtain a coating solution of the protective layer. The coating solution of the protective layer was sprayed onto the enteric-coated pellet through a GLATT GPCG-1 fluidized bed.

The formula B1 of the protective layer was referred to for specific process parameters.

4) Formula B4 of the Protective Layer (Unit: g)

| | |
|---|---|
| Ilaprazole enteric-coated pellet | 100 |
| Hydroxypropylcellulose-SSL | 2.5 |
| Talc | 1.2 |
| Purified water | 50 |

Preparation Process:

2.5 g of hydroxypropylcellulose-SSL according to the formula was weighed and dissolved in 50 g of purified water, and then 1.2 g of talc was added and uniformly dispersed at a high shear rate of 5000 rpm to obtain a coating solution of the protective layer. The coating solution of the protective layer was sprayed onto the enteric-coated pellet through a GLATT GPCG-1 fluidized bed.

The formula B1 of the protective layer was referred to for specific process parameters.

5) Formula B5 of the Protective Layer (Unit: g)

| | |
|---|---|
| Ilaprazole enteric-coated pellet | 100 |
| Hydroxypropylcellulose-SSL | 2.5 |
| Titanium dioxide | 1.2 |
| Purified water | 50 |

Preparation Process:

2.5 g of hydroxypropylcellulose-SSL according to the formula was weighed and dissolved in 50 g of purified water, and 1.2 g of titanium dioxide was added and dispersed at a high shear rate of 5000 rpm to obtain a coating solution of the protective layer. The coating solution of the protective layer was sprayed onto the enteric-coated pellet through a GLATT GPCG-1 fluidized bed.

The formula B1 of the protective layer was referred to for specific process parameters.

-

6) Formula B6 of the Protective Layer (for Comparative Pellet 13) (Unit: g)

| | |
|---|---|
| Ilaprazole enteric-coated pellet | 100 |
| Hydroxypropyl methylcellulose-E5 | 2.5 |
| Magnesium stearate | 0.2 |
| Purified water | 50 |

Preparation Process:

2.5 g of hydroxypropyl methylcellulose-E according to the formula was weighed and dissolved in 50 g of purified water, and then 0.2 g of magnesium stearate was added and uniformly dispersed at a high shear rate of 5000 rpm to obtain a coating solution of the protective layer. The coating solution of the protective layer was sprayed onto the enteric-coated pellet through a GLATT GPCG-1 fluidized bed.

The formula B1 of the protective layer was referred to for specific process parameters.

(II) Preparation of the Enteric-Coated Pellets

1) Preparation of the Enteric-Coated Pellets According to the Present Invention

The enteric-coated pellets A-G according to the present invention as shown in Table 1 below were prepared according to the formulas of the component layers of the enteric-coated pellets as listed in the above section (I).

TABLE 1

Formulas of the enteric-coated pellets (tablets) A-G according to the present invention

| | Pellet A | Pellet B | Pellet C | Pellet D | Pellet E | Pellet F | Pellet G |
|---|---|---|---|---|---|---|---|
| Drug-containing pellet | W1 | W2 | W3 | W4 | W5 | W11 | W12 |
| Isolating layer | G2 | G1 | G2 | G2 | G2 | G2 | G2 |
| Enteric coating layer | C1 | C1 | C1 | C1 | C1 | C1 | C1 |
| Protective layer | B1 | B2 | B3 | B4 | B5 | B2 | B1 |
| | Tableting and coating | | | | | | |
| Pellet tablet | Pellet tablet A | Pellet tablet B | Pellet tablet C | Pellet tablet D | Pellet tablet E | Pellet tablet F | Pellet tablet G |
| Drug-loading rate (%) of the drug-containing pellet | 95.6 | 91.4 | 92.4 | 93.3 | 94.1 | 92.5 | 93.8 |

where the drug-applying rate $W_x$ of the drug-containing pellet=(actual content of drug-containing pellet)/(theoretical content of drug-containing pellet)×100%

2) Preparation of the Comparative Pellets 3-16

The comparative pellets 3-15 as shown in Tables 2-1 and 2-2 below were prepared according to the formulas of the component layers of the enteric-coated pellets as listed in the above section (I).

TABLE 2-1

Formulas of the comparative pellets (tablets) 5-10 and 14-15 mainly used for the study on the isolating layer

| Comparative pellet | 5 | 6 | 7 | 8 | 9 | 10 | 14 | 15 |
|---|---|---|---|---|---|---|---|---|
| Drug-containing pellet | W1 | W1 | W1 | W1 | W1 | W1 | W1 | W1 |
| Isolating layer | G6 | G7 | G3 | G8 | G4 | G5 | G9 | G12 |
| Enteric coating layer | C1 | C1 | C1 | C1 | C1 | C1 | C1 | C1 |

TABLE 2-1-continued

| Formulas of the comparative pellets (tablets) 5-10 and 14-15 mainly used for the study on the isolating layer | | | | | | | | |
|---|---|---|---|---|---|---|---|---|
| Comparative pellet | 5 | 6 | 7 | 8 | 9 | 10 | 14 | 15 |
| Protective layer | B1 | B1 | B1 | B1 | B1 | B1 | B1 | B1 |
| Particle size D90 of ilaprazole | 46.8 μm* | | | | | | | |
| | Tableting and coating | | | | | | | |
| | Comparative pellet tablet 5 | Comparative pellet tablet 6 | Comparative pellet tablet 7 | Comparative pellet tablet 8 | Comparative pellet tablet 9 | Comparative pellet tablet 10 | Comparative pellet tablet 14 | Comparative pellet tablet 15 |

*In order to facilitate the comparison between the data, ilaprazole with a uniform particle size D90 was used here. According to the present invention, those skilled in the art will understand that the particle size D90 is not limited thereto.

TABLE 2-2

| Formulas of the comparative pellets (tablets) 3-4, 11-13 and 16-18 mainly used for the study on the component layers of the enteric-coated pellets | | | | | | | | |
|---|---|---|---|---|---|---|---|---|
| Comparative pellet | 3 | 4 | 11 | 12 | 13 | 16 | 17 | 18 |
| Drug-containing pellet | W8 | W9 | W6 | W1 | W1 | W7 | W10 | W13 |
| Isolating layer | G2 | G2 | G2 | G2 | G2 | G2 | G2 | G2 |
| Enteric coating layer | C1 | C1 | C1 | C1 | C1 | C1 | C1 | C1 |
| Protective layer | B1 | B1 | B1 | None | B6 | B1 | B1 | B2 |
| Particle size D90 of Ilaprazole | 82.5 μm* | 105.6 μm* | 46.8 μm* | | | ≤50 μm* | | |
| | Comparative pellet tablet 3 | Comparative pellet tablet 4 | Comparative pellet tablet 11 | Comparative pellet tablet 12 | Comparative pellet tablet 13 | Comparative pellet tablet 16 | Comparative pellet tablet 17 | Comparative pellet tablet 18 |

*In order to facilitate the comparison between the data, ilaprazole with a uniform particle (or specific) size D90 was used here. According to the present invention, those skilled in the art will understand that the particle size D90 is not limited thereto.

Example 2. Preparation of Enteric-Coated Pellet Tablets

In this example, the enteric-coated pellets A-G according to the present invention and the comparative pellets 3-18 prepared in Example 1 were prepared into the enteric-coated pellet tablets A-G according to the present invention and the comparative pellet tablets 3-18. In addition, the comparative pellet tablet 1 (according to CN 1134666 A) and the comparative pellet tablet 2 (according to CN 102525990 A) were also prepared according to the method for preparing the enteric-coated pellet tablets in the prior art, with ilaprazole (particle size D90 of 46.8 μm, to facilitate the comparison between the data) serving as the pharmaceutically active substance.

2.1 Preparation of the Enteric-Coated Pellet Tablets A-G According to the Present Invention and Comparative Pellet Tablets 3-18

The enteric-coated pellets shown in Table 1 above as well as Tables 2-1 and 2-2 above were prepared into the enteric-coated pellet tablets by the following tableting and coating steps respectively.

1) Preparation of the Pellet Tablet (Unit: g)

| | |
|---|---|
| Ilaprazole outer coated pellet | 200 |
| Microcrystalline cellulose PH102 | 339.2 |
| Crospovidone-XL | 113.1 |
| Sodium stearyl fumarate | 12.8 |

Preparation Process of the Tablets:

The ilaprazole enteric outer coated pellets, microcrystalline cellulose PH102, crospovidone-XL, and sodium stearyl fumarate according to the above formula were added in a 3 L hopper mixer, and the mixture was mixed for 15 min at 10 rpm. Then the mixture was placed in a tablet press for tableting to obtain the tablets with the hardness of 8-12 kg, and the weight equivalent to 5 mg of ilaprazole contained in each tablet.

2) Pellet Tablet Coating (Unit: g)

| | |
|---|---|
| Pellet tablet | 400 |
| Opadry coating powder | 20 |
| Purified water | 166.5 |

Preparation Process of the Coating:

20 g of Opadry coating solution was weighed and dissolved in 166.5 g of purified water, and the ilaprazole pellet tablets were coated using an efficient coating pan.

2.2 Preparation of Comparative Pellet Tablet 1:

Comparative pellet tablet 1 was prepared according to the method and process for preparing enteric-coated pellet tablets described in Example 16 of CN 1134666 A, using the outer coating described in Example 15 thereof, with ilaprazole serving as the pharmaceutically active substance and a surfactant added to the drug-loading layer. The method is specified as follows:

1) Preparation of the Drug-Containing Pellet

Formula of the Drug-Containing Pellet (Unit: g)

| | |
|---|---|
| Sucrose pellet core | 100 |
| Ilaprazole | 148 |
| Hydroxypropyl methylcellulose-E5 | 22 |
| Polysorbate-80 | 3 |
| Purified water | 700 |

Preparation Process:

150 g of hydroxypropyl methylcellulose-E5 and 3 g of tween-80 were weighed and dissolved in purified water to obtain a hydroxypropyl methylcellulose binder solution, and the ilaprazole starting material with a particle size D90 less than 50 m was dispersed into the binder and dispersed for 5 min at 10,000 rpm, and then the ilaprazole suspension was sprayed onto the sucrose pellet core through a GLATT GPCG-1 fluidized bed.

The specific process parameters were as follows:

| Parameters | Preheating | Drug applying | Drying |
|---|---|---|---|
| Inlet air volume ($m^3$/min) | 45 | 50-80 | 60 |
| Inlet air temperature (° C.) | 40-50 | 40-50 | 40-50 |
| Material temperature (° C.) | 38-40 | 35-40 | 35-40 |
| Atomizing pressure (bar) | 0.1 | 0.1-0.2 | 0.1 |
| Spraying rate (g/min) | | 0.5-4 | |

2) Preparation of the Isolated Pellet

Formula of the Isolated Pellet (Unit: g)

| | |
|---|---|
| Ilaprazole-containing pellet | 103 |
| Hydroxypropylcellulose-SSL | 11 |
| Talc | 42.5 |
| Magnesium stearate | 2.75 |
| Purified water | 387.5 |

Preparation Process:

103 g of hydroxypropylcellulose-SSL was weighed and dissolved in 387.5 g of purified water to obtain a hydroxypropylcellulose binder solution, and 42.5 g of talc and 2.75 g of magnesium stearate were added to the binder solution and dispersed for 5 min at a high shear rate of 10,000 rpm, and then the coating solution of an isolating layer was sprayed onto the ilaprazole-containing pellet through a GLATT GPCG-1 fluidized bed. The specific process parameters were as follows:

| Parameters | Preheating | Drug applying | Drying |
|---|---|---|---|
| Inlet air volume ($m^3$/min) | 45 | 50-80 | 60 |
| Inlet air temperature (° C.) | 40-50 | 40-50 | 40-50 |
| Material temperature (° C.) | 38-40 | 35-40 | 35-40 |
| Atomizing pressure (bar) | 0.1 | 0.1-0.2 | 0.1 |
| Spraying rate (g/min) | | 0.5-4 | |

3) Preparation of the Enteric-Coated Pellet

Formula of the Enteric-Coated Pellet (Unit: g)

| | |
|---|---|
| Ilaprazole magnesium isolated pellet | 127.3 |
| Eudragit L30D-55 | 127 |
| Glyceryl monostearate | 1.9 |
| Triethyl citrate | 3.8 |
| Polysorbate-80 | 1.8 |
| Purified water | 50 |

Preparation Process:

1.8 g of polysorbate-80, 3.8 g of triethyl citrate and 1.9 g of glyceryl monostearate were weighed and dissolved in 50 g of purified water at 70° C., dispersed for 5 min at a high shear rate of 5000 rpm, and left to stand to room temperature; 127 g of Eudragit L30D-55 was added and the mixture was stirred for 45 min for later use; and the enteric coating solution was sprayed onto the isolated pellet through a GLATT GPCG-1 fluidized bed.

The specific process parameters were as follows:

| Parameters | Preheating | Enteric coating | Drying |
|---|---|---|---|
| Inlet air volume ($m^3$/min) | 50 | 50-80 | 60 |
| Inlet air temperature (° C.) | 35-30 | 33-42 | 35-45 |
| Material temperature (° C.) | 25-30 | 25-30 | 30-35 |
| Atomizing pressure (bar) | 0.1 | 0.15-0.25 | 0.1 |
| Spraying rate (g/min) | | 0.5-3 | |

4) Preparation of the Protective Layer Pellet

Formula of the Protective Layer (Unit: g)

| | |
|---|---|
| Ilaprazole enteric-coated pellet | 171.3 |
| Hydroxypropyl methylcellulose-E5 | 2.5 |
| Magnesium stearate | 0.08 |
| Purified water | 51.3 |

Preparation Process:

2.5 g of hydroxypropyl methylcellulose-E5 was weighed and dissolved in 51.3 g of purified water, and then 0.08 g of magnesium stearate was added and uniformly dispersed at a high shear rate of 5000 rpm to obtain a coating solution of the protective layer. The coating solution of the protective layer was sprayed onto the enteric-coated pellet through a GLATT GPCG-1 fluidized bed.

The specific process parameters were as follows:

| Parameters | Preheating | Isolating coating | Drying |
|---|---|---|---|
| Inlet air volume ($m^3$/min) | 60 | 60-90 | 80 |
| Inlet air temperature (° C.) | 40-50 | 45-55 | 45-55 |
| Material temperature (° C.) | 38-40 | 35-40 | 35-40 |
| Atomizing pressure (bar) | 0.1 | 0.1-0.2 | 0.1 |
| Spraying rate (g/min) | | 0.6-4.5 | |

5) Preparation of the Pellet Tablet (Unit: g)

| | |
|---|---|
| Ilaprazole enteric-coated pellet | 173.9 |
| Microcrystalline cellulose PH102 | 869.5 |

-continued

| | |
|---|---|
| Crospovidone | 17.39 |
| Sodium stearyl fumarate | 17.39 |

Preparation Process of the Tablets:

The ilaprazole enteric-coated pellets, microcrystalline cellulose, crospovidone and sodium stearyl fumarate according to the above formula were added into a 3 L hopper mixer, and the mixture was mixed for 15 min at 10 rpm. Then the mixture was placed in a tablet press for tableting to obtain the tablets with the hardness of 8-12 kg, and the weight equivalent to 5 mg of ilaprazole contained in each tablet.

6) Preparation of the Pellet Tablet Coating (Unit: g)

| | |
|---|---|
| Pellet tablet | 1000 |
| Opadry coating powder | 40 |
| Purified water | 333 |

40 g of Opadry coating solution was weighed and dissolved in 333 g of purified water, and the ilaprazole pellet tablets were coated using an efficient coating pan. The comparative pellet tablet 1 was prepared.

2.3 Preparation of Comparative Pellet Tablet 2:

Comparative pellet 2 was prepared according to the method for preparing enteric-coated pellet tablets described in CN 102525990 A, with ilaprazole serving as the pharmaceutically active substance.

1) Preparation of the Drug-Containing Pellet Core

Formula of the Drug-Containing Pellet Core (Unit: g)

| | |
|---|---|
| Sucrose pellet core | 300 |
| Ilaprazole | 30 |
| Magnesium oxide | 3 |
| Hydroxypropyl methylcellulose | 10 |
| 80% (v/v) aqueous ethanol solution | 850 |

Preparation Process:

Blank sucrose pellet cores (0.25-0.3 mm) were sieved through a 50 mesh sieve and a 60 mesh sieve respectively, and the pellets between 50 mesh and 60 mesh were applied with drug. The method for preparing a drug-applying solution: hydroxypropyl methylcellulose and magnesium oxide according to the formula were dissolved in 80% (v/v) aqueous ethanol solution, and the resulting solution was adjusted to about pH 12 with 4% (m/v) sodium hydroxide solution; and then ilaprazole according to the formula was added, and the mixture was uniformly stirred. The viscosity of the drug-applying solution was 13.22 cp.

The specific process parameters were as follows:

| Parameters | Preheating | Drug applying | Drying |
|---|---|---|---|
| Time (min) | 5 | 160-200 | 20 |
| Inlet air volume ($m^3$/min) | 60-80 | 70-90 | 60-80 |
| Inlet air temperature (° C.) | 40-50 | 40-50 | 40-50 |
| Outlet air temperature (° C.) | 25-40 | 23-38 | 38-45 |
| Material temperature (° C.) | 28-35 | 28-35 | 35-45 |
| Filter bag shaking time (s) | 2-5 | 5-10 | 5-10 |
| Atomizing pressure (bar) | 0.1-0.3 | 0.2-1.2 | 0.2-0.5 |
| Spraying rate (g/mL) | | 1-15 | |
| Pump rotation speed (L/min) | | 5-9 | |
| Spraying process | | Continuous operation | |

310 g of light yellow ilaprazole pellets were prepared, with a yield of 90.3%.

2) Preparation of the Isolated Pellet

Formula of the Isolated Pellet (Unit: g)

| | |
|---|---|
| Ilaprazole-containing pellet | 300 |
| HPMC 5CP | 15 |
| Talc | 50 |
| 80% v/v aqueous ethanol solution | 535 |

Preparation Process:

300 g of drug-containing pellets were coated with the isolating layer solution after the pH of the isolating solution was adjusted to be more than 10.5, wherein the viscosity of the isolating solution was 15.24 cp. The operation parameters were shown in the following table:

| Parameters | Preheating | Drug applying | Drying |
|---|---|---|---|
| Time (min) | 5 | 40-60 | 30 |
| Inlet air volume ($m^3$/min) | 50-70 | 60-100 | 50-60 |
| Inlet air temperature (° C.) | 40-50 | 40-55 | 50-55 |
| Outlet air temperature (° C.) | 25-40 | 23-38 | 38-45 |
| Material temperature (° C.) | 30-40 | 35-45 | 40 |
| Filter bag shaking time (s) | 1-10 | 5-30 | 5-30 |
| Atomizing pressure (bar) | 0.3 | 0.3-1.3 | 0.5 |
| Spraying rate (g/mL) | | 5-15 | |
| Pump rotation speed (L/min) | | 3-7 | |
| Spraying process | | Continuous operation | |

345 g of pellets were prepared, with a yield of 94.5%.

3) Preparation of the Enteric-Coated Pellet

Formula of the Enteric-Coated Pellet (Unit: g)

| | |
|---|---|
| Ilaprazole isolated pellet | 150 |
| Eudragit L30D-55 | 180 |
| Polyethylene glycol 6000 | 10 |
| Tween-80 | 0.3 |
| Water | 200 |

Preparation Process:

6.5 mL of 4% (m/v) aqueous sodium hydroxide solution was added to Eudragit L30D-55, polyethylene glycol 6000 was added with stirring, and the mixture was sieved through an 80 mesh sieve. The isolated pellets were coated with the enteric coating. The main parameters were as follows: the material temperature was 25-30° C., the inlet air temperature was 28-35° C., the spraying speed was 10-30 rpm, and the fan frequency was 30-40. 214.1 g of pellets were prepared, with a yield of 99.9%.

4) Preparation of the Pellet Tablet

Formula of the Pellet Tablet (Unit: g)

| | |
|---|---|
| Ilaprazole enteric-coated pellet | 150 |
| Pregelatinized starch | 50 |
| Starch | 50 |
| Mannitol | 50 |
| Microcrystalline cellulose PH101 | 240 |
| 4% starch slurry | 10 |

The materials were mixed according to formula in the table, and subjected to tableting to obtain the tablets, with each weighing 314.9 mg. The comparative pellet tablet 2 was prepared.

Example 3. Preparation of Enteric-Coated Pellet Capsules 600 g of ilaprazole protective layer-coated pellets A ($W_1$+$G_2$+$C_1$+$B_1$) were loaded into NO. 3 capsule shells by a capsule filler, with each capsule containing 5 mg of ilaprazole.

Example 4. Performance Test of Enteric-Coated Pellet Tablets and Capsules

In the example 4, the enteric-coated pellet tablets and capsules prepared in the above examples were tested for content, dissolution rate, related substances, etc., and comparative pellets 3-16 were compared in terms of the test results, with the pellet tablet A according to the present invention serving as a reference. The test method is specified as follows:

1. Determination of Content

1) Operation method: General Chapter 0512, *Chinese Pharmacopoeia*, Volume IV, 2015 Edition was referred to for general methods.

Specifically, the method comprises the following steps:

Preparation of the sample solution: 5 mL of the sample solution according to the section of related substance test was precisely measured, placed in a 50 mL measuring flask, diluted to volume with mobile phase, shaken and filtered, and the subsequent filtrate was used as the sample solution.

Preparation of the control solution: a proper amount of ilaprazole control was precisely weighed and dissolved with a diluent, and the resulting solution was diluted with the diluent to a solution containing about 20 μg of the ilaprazole control per 1 mL. The diluted solution was used as the control solution.

System suitability solution: an appropriate amount of impurity I (ilaprazole sulfone, chemical name: 2-[[(4-methoxy-3-methyl)-2-pyridyl]methyl]-sulfonyl-5-(1H-pyrrol-1-yl)-1H-benzimidazole) control and ilaprazole control were weighed and dissolved with a diluent, and the resulting solution was diluted with the diluent to a solution containing 20 μg of the impurity I and ilaprazole per 1 mL.

Chromatographic conditions: octadecylsilane chemically bonded silica was used as a filler, 400 mL of acetonitrile was diluted with a phosphate buffer (2.28 g of dipotassium hydrogen phosphate was dissolved in water, and the resulting solution was diluted with water to 1000 mL and adjusted to pH 7.5 with phosphoric acid) to 1000 mL for use as a mobile phase, the flow rate was 1.0 mL/min, the detection wavelength was 237 nm, and the column temperature was 25° C.

System suitability requirement: in the chromatogram of the system suitability solution, the theoretical number of plates should be not less than 2500 calculated according to the ilaprazole peak, and the resolution between the impurity I peak and the ilaprazole peak should be in accordance with the standard.

Determination method: 20 μL of each of the control solution and the sample solution was measured precisely and injected into the liquid chromatograph, and the chromatogram was recorded.

2) Calculation method: the average content of 10 tablets was calculated according to peak area by external standard method.

3) Standard: the content of ilaprazole (C19H18N4O2S) should be 90.0%-110.0% of the labeled amount.

2. Determination of Dissolution Rate

1) Operation method: the dissolution rate was determined according to the content homogeneity inspection method (Method 1 of the second method of General Chapter 0931, *Chinese Pharmacopoeia*, Volume IV, 2015 Edition was referred to for general methods). Specifically, the method comprises the following steps:

According to the content homogeneity inspection method, the product was dissolved in 300 mL of 0.1 mol/L hydrochloric acid solution (dissolution medium, 9.0 mL of hydrochloric acid was diluted with water to 1000 mL), and the rotation speed was 100 rpm; after 120 min, 700 mL of 0.086 mol/L disodium hydrogen phosphate solution (30.8 g of disodium hydrogen phosphate and 7 g of tween-80 was diluted with water to 1000 mL) preheated to 37±0.5° C. was immediately added to the dissolution cup, and uniformly mixed at a constant rotation speed according to the method; and after 45 min, the mixture was sampled.

Sample solution: a proper amount of dissolution solution was filtered, and 5 mL of subsequent filtrate was precisely measured; and 1 mL of 0.15 mol/L sodium hydroxide solution was added immediately and precisely, shaken uniformly and filtered, and the subsequent filtrate was used as the sample solution.

Control solution: about 10 mg of ilaprazole control was precisely weighed, added to a 20 mL measuring flask, dissolved with a proper amount of acetonitrile, diluted to volume with acetonitrile, and shaken uniformly; 1 mL of the diluted solution was precisely measured, placed in a 100 mL measuring flask, diluted to volume with a phosphate buffer solution (pH 6.8) (700 mL of 0.086 mol/L disodium hydrogen phosphate solution was uniformly mixed with 300 mL of 0.1 mol/L hydrochloric acid solution) and shaken uniformly; 5 mL of the diluted solution was precisely weighed, 1 mL of 0.05 mol/L sodium hydroxide solution was immediately and precisely added, the resulting mixture was shaken uniformly and filtered, and the subsequent filtrate was taken as the control solution.

The dissolution amount of each tablet was calculated according to the method described in the section of determination of content.

3. Related Substance Test

1) Operation method: the related substances were measured according to the high performance liquid chromatography (General Chapter 0512, *Chinese Pharmacopoeia*, Volume IV, 2015 Edition was referred to general methods). Specifically, the method comprises the following steps:

Diluent: 0.05 mol/L sodium hydroxide-methanol-water=50:20:30

Sample solution: 10 tablets of the product were added to a 250 mL measuring flask, 125 mL of 0.05 mol/L sodium hydroxide solution was added, and the resulting mixture was shaken in an oscillator (250 rpm) for 20 min; and 50 mL of methanol was added and the resulting mixture was sonicated for 10 min, diluted to volume with water, shaken uniformly, and centrifuged to obtain the supernatant.

Control solution: a proper amount of the sample solution was precisely measured and diluted with a diluent to obtain a solution containing about 1 μg of ilaprazole per 1 mL.

Sensitivity solution: 1 mL of the control solution was precisely measured, added to a 10 mL measuring flask, diluted to volume with a diluent, and shaken uniformly.

Impurity I control stock solution: about 6 mg of impurity I was added to a 100 mL measuring flask and diluted to volume with a diluent.

System suitability solution: about 3 mg of ilaprazole control was added to a 10 mL measuring flask, and dissolved in a proper amount of diluent; and 1 mL of impurity I control stock solution was precisely added, and the resulting mixture was diluted to volume with a diluent, and shaken uniformly.

Chromatographic conditions: octadecylsilane chemically bonded silica was used as a filler (Gemini-NX C18 150×4.6 mm, 5 m or an equivalent chromatographic column), 0.01 mol/L dipotassium hydrogen phosphate solution (adjusted to pH 7.5 with 10% phosphoric acid) was used as mobile phase A, acetonitrile was used as mobile phase B, and linear gradient elution was performed according to the following table; the flow rate was 1.0 mL/min; the detection wavelength was 237 nm; and the column temperature was 25° C.

| Time (min) | Mobile phase A (%) | Mobile phase B (%) |
|---|---|---|
| 0 | 77 | 23 |
| 5 | 66 | 34 |
| 15 | 50 | 50 |
| 40 | 50 | 50 |
| 40.5 | 77 | 23 |
| 50 | 77 | 23 |

System suitability solution requirement: in the chromatogram of the system suitability solution, the resolution between the impurity I peak and the ilaprazole peak should be more than 2.0. In the chromatogram of the sensitivity solution, the signal-to-noise ratio of the peak height of the ilaprazole peak should be greater than 10.

Determination method: 20 μL of each of the sample solution and the control solution was measured and injected into the liquid chromatograph, and the chromatogram was recorded.

4.1 Stability Test and Acid Resistance Test of the Enteric-Coated Pellet Tablets and Capsules According to the Present Invention 1) In this example, then enteric-coated pellet tablets A-G according to the present invention and the capsule of Example 3 were subjected to the accelerated stability test. The method is specified as follows:

Test protocol: the enteric-coated pellet tablets A-G and the capsule of Example 3 were packaged in HDPE bottles of 14 tablets (capsules) respectively, and the packaged pellet tablets or capsules were placed in an accelerated stability test chamber at 40° C./RH75%, and sampled after 1/3/6 months for detecting related substances of the enteric-coated pellet tablets or capsules with different formulas. The stability data of the enteric-coated pellet tablets A-G and the capsule of Example 3 obtained by the test are shown in Table 3-1 below:

TABLE 3-1

Stability data of the enteric-coated pellet tablets A-G according to the present invention and the capsule of Example 3

| Time | Pellet tablet A | Pellet tablet B | Pellet tablet C | Pellet tablet D | Pellet tablet E | Pellet tablet F | Pellet tablet G | Capsule |
|---|---|---|---|---|---|---|---|---|
| Day 0 | 0.12% | 0.16% | 0.19% | 0.15% | 0.13% | 0.18% | 0.26% | 0.20% |
| Month 1 | 0.15% | 0.22% | 0.26% | 0.24% | 0.20% | 0.36% | 0.54% | 0.34% |
| Month 3 | 0.36% | 0.25% | 0.89% | 0.77% | 0.97% | 0.47% | 0.87% | 0.58% |
| Month 6 | 0.87% | 1.07% | 1.28% | 0.82% | 0.99% | 0.68% | 1.02% | 0.98% |

As can be seen from Table 3-1, the pellet tablets A-G and the capsule prepared from the enteric-coated pellets according to the present invention had good stability with total impurity content not exceeding 1.5%.

2) In this example, the enteric-coated pellet tablets A-G according to the present invention and the capsule of Example 3 were subjected to the acid resistance test. The method is specified as follows: according to the method, 6 tablets of each of the enteric-coated pellet tablets A-G and the capsule were dissolved in 300 mL of 0.1 mol/L hydrochloric acid solution (dissolution medium, 9.0 mL of hydrochloric acid was diluted with water to 1000 mL), and the rotation speed was 100 rpm; after 120 min, the dissolution cups were taken out, the hydrochloric acid was filtered off using a suction filtration device, and the remaining pellets were collected in a 50 mL volumetric flask; 20 mL of 0.05 mol/L sodium hydroxide solution was added, and the resulting mixture was shaken in an oscillator (250 rpm) for 20 min; and 30 mL of methanol was added, and the resulting mixture was sonicated for 10 min, diluted to volume with water, shaken uniformly, and centrifuged to obtain the supernatant. The remaining drug content in the pellets, i.e. the acid resistance of the samples, was determined.

TABLE 3-2

Acid resistance data of the enteric-coated pellet tablets A-G according to the present invention and the capsule of Example 3

| Time | Pellet tablet A | Pellet tablet B | Pellet tablet C | Pellet tablet D | Pellet tablet E | Pellet tablet F | Pellet tablet G | Capsule |
|---|---|---|---|---|---|---|---|---|
| Day 0 | 99.6% | 99.1% | 97.9% | 96.5% | 97.4% | 98.4% | 98.7% | 96.8% |
| Month 1 | 98.8% | 98.6% | 98.2% | 96.8% | 97.8% | 98.2% | 98.5% | 96.3% |

TABLE 3-2-continued

Acid resistance data of the enteric-coated pellet tablets A-G according to the present invention and the capsule of Example 3

| Time | Pellet tablet A | Pellet tablet B | Pellet tablet C | Pellet tablet D | Pellet tablet E | Pellet tablet F | Pellet tablet G | Capsule |
|---|---|---|---|---|---|---|---|---|
| Month 3 | 98.3% | 97.9% | 98.1% | 95.9% | 98.2% | 98.1% | 97.8% | 97.2% |
| Month 6 | 98.2% | 98.0% | 97.6% | 95.6% | 97.5% | 97.6% | 97.9% | 96.6% |

As can be seen from Table 3-2, the pellet tablets A-G and the capsule prepared from the enteric-coated pellets according to the present invention both had good acid resistance of above 90%.

4.2 Stability Test and Acid Resistance Test of the Enteric-Coated Pellet Tablets In this example, taking an enteric-coated pellet tablet as an example, the effects of the components and the proportions thereof of the enteric-coated pellet tablets on their stability and acid resistance were compared.

4.2.1 Effect of the Ingredients of the Isolating Layer Comprised in the Enteric-Coated Pellets 1) Comparison between the enteric-coated pellet tablet A according to the present invention and the comparative pellet tablets 5, 6, 9, 10 and 14 in terms of the stability In this example, the enteric-coated pellet tablet A according to the present invention and the comparative pellet tablets 5, 6, 9, 10 and 14 were subjected to the accelerated stability test. In this test, compared to the enteric-coated pellet tablet A according to the present invention, the comparative pellet tablet 5 had only one inert substance isolating layer comprising no alkaline compound; the comparative pellet tablets 6, 9, 10 and 14 all had a first isolating layer closely adjacent to the pellet core and a second isolating layer closely adjacent to the enteric coating layer; however, in the comparative pellet tablet 6, the first isolating layer comprised a binder and an anti-adherent, but did not comprise an alkaline compound; in the comparative pellet tablet 9, the first isolating layer was a mixed layer (which refers to a layer comprising, in addition to the binder, an alkaline compound and a water-insoluble inert substance capable of preventing the pellets from adhesion), and comprised a water-insoluble alkaline compound as an alkaline compound; in the comparative pellet tablet 10, the first isolating layer was an alkaline layer mainly comprising a binder and a water-soluble alkaline compound; and in the comparative pellet 14, the first isolating layer was a mixed layer, and comprised a water-soluble alkaline compound as an alkaline compound.

Test protocol: the enteric-coated pellet tablet A according to the present invention and the comparative pellet tablets 5, 6, 9, 10 and 14 were packaged in HDPE bottles of 14 tablets respectively, and the packaged pellet tablets were placed in an accelerated stability test chamber at 40° C./RH75%, and sampled after 1/3/6 months for detecting related substances of the pellet tablets with different formulas. The stability data of the pellet tablets obtained by the test are shown in Table 4-1 below:

TABLE 4-1

Stability data of the pellet tablet A according to the present invention and the comparative pellet tablets 5, 6, 9, 10 and 14

| Time | Pellet tablet A | Comparative pellet tablet 5 | Comparative pellet tablet 6 | Comparative pellet tablet 9 | Comparative pellet tablet 10 | Comparative pellet tablet 14 |
|---|---|---|---|---|---|---|
| Day 0 | 0.12% | 0.35% | 0.89% | 0.24% | 0.20% | 0.49% |
| Month 1 | 0.15% | 0.72% | 1.26% | 0.63% | 0.43% | 0.61% |
| Month 3 | 0.36% | 1.25% | 1.89% | 0.96% | 0.66% | 1.05% |
| Month 6 | 0.87% | 1.87% | 2.68% | 1.79% | 0.89% | 1.68% |

As can be seen from Table 4-1, the stability requirement (i.e., the total impurity content should not exceed 1.5%) cannot be met for ilaprazole with low stability when its enteric-coated pellet tablet comprises only one isolating layer (i.e., the comparative pellet tablet 5). When the enteric-coated pellet tablet comprises at least a first isolating layer and a second isolating layer, its stability can also be affected by the components of these isolating layers, for example: when the first isolating layer is a mixed layer comprising an alkaline compound and a water-insoluble inert substance capable of preventing the pellets from adhesion (i.e., the comparative pellet tablets 9 and 14), the related substances still significantly increase (the total impurity content is 1.79% and 1.68%, respectively) even under the protection of the alkaline compound, and the stability requirement cannot be met; in contrast, when the first isolating layer is an alkaline layer comprising an alkaline compound and not comprising a water-insoluble inert substance capable of preventing the pellets from adhesion (e.g., the pellet tablet A and the comparative pellet tablet 10), the enteric-coated pellet tablet has good stability; in addition, the stability requirement (i.e., the total impurity content should not exceed 1.5%) cannot be met for ilaprazole with low stability when its enteric-coated pellet tablet comprises the alkaline compound only in the pellet core (i.e., the comparative pellet tablet 6).

2) Comparison between the enteric pellet tablet A according to the present invention and the comparative pellet tablets 10, 14 and 15 in terms of the acid resistance. In this example, the enteric-coated pellet tablet A according to the present invention and the comparative pellet tablets 10, 14 and 15 were subjected to the acid resistance test. In this test, the comparative pellet tablet 15 differed from the enteric-coated pellet tablet A according to the present invention in that: the second isolating layer of the comparative pellet tablet 15 did not comprise a water-insoluble inert substance capable of preventing the pellets from adhesion. The method is specified as follows:

the enteric-coated pellet tablet A according to the present invention and the comparative pellet tablets 10, 14 and 15 were packaged in HDPE bottles of 14 tablets, respectively; and the packaged pellet tablets were placed in an accelerated stability test chamber at 40° C./RH75%, and sampled after 1/3/6 months; then according to the method, the tablets were dissolved in 300 mL of 0.1 mol/L hydrochloric acid solution (dissolution medium, 9.0 mL of hydrochloric acid was diluted with water to 1000 mL), and the rotation speed was 100 rpm; after 120 min, the dissolution cups were taken out, the hydrochloric acid was filtered off using a suction filtration device, and the remaining pellets were collected in a 50 mL volumetric flask; 20 mL of 0.05 mol/L sodium hydroxide solution was added, and the resulting mixture was shaken in an oscillator (250 rpm) for 20 min; and 30 mL of methanol was added, and the resulting mixture was sonicated for 10 min, diluted to volume with water, shaken uniformly, and centrifuged to obtain the supernatant. The remaining drug content in the pellets, i.e. the acid resistance of the samples, was determined. The acid resistance data of the pellet tablets obtained by the test are shown in Table 4-2 below:

TABLE 4-2

Acid resistance data of the enteric-coated pellet tablet A according to the present invention and the comparative pellet tablets 10, 14 and 15

| Time | Pellet tablet A | Comparative pellet tablet 10 | Comparative pellet tablet 14 | Comparative pellet 15 |
|---|---|---|---|---|
| Day 0 | 96.7% | 96.2% | 95.3% | 97.9% |
| Month 1 | 95.9% | 95.6% | 92.1% | 97.6% |
| Month 3 | 95.5% | 92.1% | 87.5% | 95.5% |
| Month 6 | 95.3% | 85.6% | 82.5% | 96.3% |

As can be seen from the results shown in Table 4-2, the comparative pellet tablet (e.g., the comparative pellet tablet 14) which already had lower stability in the stability test also had lower acid resistance under accelerated conditions; the comparative pellet tablet 10 having the first isolating layer comprising a different type of the alkaline compound (i.e., a water-soluble alkaline compound) became less acid resistant (the content of the remaining ilaprazole in the comparative pellet tablet 10 at month 6 was 85.6%) as compared to the enteric-coated pellet tablet A according to the present invention, and the acid resistance was lower than the required standard (i.e., the acid resistance average of 6 tablets should be not less than 90%). That is, although the alkaline compound can provide the enteric-coated pellet tablet with good stability when used as the first isolating layer, the type of the alkaline compound will affect the acid resistance of the enteric-coated pellet tablet. Compared to the first isolating layer comprising a water-soluble alkaline compound, the isolating layer comprising a water-insoluble alkaline compound can improve and enhance the acid resistance of the enteric-coated pellet tablet when used as the first isolating layer of the enteric-coated pellet tablet. In addition, it can also be seen from Table 4-2 that the acid resistance of the comparative pellet tablet 15 in which the second isolating layer does not comprise a water-insoluble inert substance capable of preventing the pellets from adhesion is not affected.

In summary, with respect to the components of the various isolating layers comprised in the enteric-coated pellet, at least two isolating layers are provided, and for the first isolating layer closely adjacent to the pellet core, when the first isolating layer comprises a water-insoluble alkaline compound, and does not comprise a water-soluble alkaline compound and a water-insoluble inert substance capable of preventing the pellets from adhesion, the ilaprazole enteric-coated pellet tablet prepared from the enteric-coated pellets can have both good stability and acid resistance.

4.2.2 Effect of the Proportions of the Components of the Isolating Layer Comprised in the Enteric-Coated Pellets According to the Present Invention 1) Comparison between the enteric-coated pellet tablet A according to the present invention and the comparative pellet tablets 7 and 8 in terms of the stability In this example, the enteric-coated pellet tablet A according to the present invention and the comparative pellet tablets 7 and 8 were subjected to the accelerated stability test. In this test, compared to the enteric-coated pellet tablet A according to the present invention, the comparative pellet tablet 7 has a larger amount of the water-insoluble alkaline compound comprised in the first isolating layer; for example, when the amount of ilaprazole is 10 parts, the amount of the water-insoluble alkaline compound comprised in the first isolating layer is more than 36 parts; the comparative pellet tablet 8 has a larger amount of the anti-adherent (equivalent to the water-insoluble inert substance capable of preventing the pellets from adhesion according to the present invention) comprised in the second isolating layer; and for example, when the amount of ilaprazole is 10 parts, the amount of the anti-adherent in the second isolating layer is more than 44 parts.

The method is specified as follows:

the enteric-coated pellet tablet A according to the present invention and the comparative pellet tablets 7 and 8 were packaged in HDPE bottles of 14 tablets respectively, and the packaged pellet tablets were placed in an accelerated stability test chamber at 40° C./RH75%, and sampled after 1/3/6 months for detecting related substances of the enteric-coated pellet tablets with different formulas. The stability data of the enteric-coated pellet tablets obtained by the test are shown in Table 5-1 below:

TABLE 5-1

Stability data of the enteric-coated pellet tablet A according to the present invention and the comparative pellet tablets 7 and 8

| Time | Pellet tablet A | Comparative pellet tablet 7 | Comparative pellet tablet 8 |
|---|---|---|---|
| Day 0 | 0.12% | 0.25% | 0.23% |
| Month 1 | 0.15% | 0.34% | 0.50% |
| Month 3 | 0.36% | 0.67% | 0.87% |
| Month 6 | 0.87% | 0.92% | 0.95% |

As can be seen from the results shown in Table 5-1, the stability of the comparative pellet tablets 7 (with different proportions of components in the first isolating layer) and 8 (with different proportions of components in the second isolating layer) with different proportions of components in the isolating layers was still within the standard range (the total impurity content should not exceed 1.5%) compared to that of the enteric-coated pellet tablet A according to the present invention. That is, the change in the proportions of components in the isolating layer does not affect the stability of the enteric-coated pellet tablet.

2) Comparison between the enteric-coated pellet tablet A according to the present invention and the comparative pellet tablets 7 and 8 in terms of the acid resistance In this example, the enteric-coated pellet tablet A according to the present invention and the comparative pellet tablets 7 and 8 were subjected to the acid resistance test. The acid resistance test described in section 4.2.1 was referred to for the specific method.

The results are shown in Table 5-2 below:

TABLE 5-2

Acid resistance data of the enteric-coated pellet tablet A according to the present invention and the comparative pellet tablets 7 and 8

| Time | Pellet tablet A | Comparative pellet tablet 7 | Comparative pellet tablet 8 |
|---|---|---|---|
| Day 0 | 96.7% | 95.6% | 96.4% |
| Month 1 | 95.9% | 95.8% | 95.8% |
| Month 3 | 95.5% | 96.1% | 96.2% |
| Month 6 | 95.3% | 95.4% | 94.6% |

As can be seen from the results shown in Table 5-2, the acid resistance of the comparative pellet tablets 7 (with different proportions of components in the first isolating layer) and 8 (with different proportions of components in the second isolating layer) with different proportions of components in the isolating layers was still within the standard range (i.e., the acid resistance average of 6 tablets should be not less than 90%) compared to that of the enteric-coated pellet tablet A according to the present invention. That is, the change in the proportions of components in the isolating layer does not affect the acid resistance of the enteric-coated pellet tablet.

In summary, the change in the proportions of components in the isolating layers of the enteric-coated pellet will not affect the stability and the acid resistance of the enteric-coated pellet tablet prepared from the enteric-coated pellets.

4.2.3 Comparison Between the Enteric-Coated Pellet Tablets a, F and G According to the Present Invention and the Pellet Tablets 17 and 18 in Terms of the Acid Resistance In this example, the enteric-coated pellet tablets A, F and G according to the present invention and the pellet tablets 17 and 18 were subjected to the acid resistance test. The acid resistance test described in section 4.2.1 was referred to for the specific method.

The results are shown in Table 5-3 below:

TABLE 5-3

Acid resistance data of the enteric-coated pellet tablets A, F and G according to the present invention and the pellet tablets 17 and 18

| Time | Pellet tablet A | Pellet tablet G | Pellet tablet H | Comparative pellet tablet 17 | Comparative pellet tablet 18 |
|---|---|---|---|---|---|
| Day 0 | 96.7% | 98.4% | 98.7% | 96.1% | 97.1% |
| Month 1 | 95.9% | 98.2% | 98.5% | 92.4% | 96.5% |
| Month 3 | 95.5% | 98.1% | 97.8% | 90.5% | 95.6% |
| Month 6 | 95.3% | 97.6% | 97.9% | 88.1% | 94.8% |

As can be seen from the results shown in Table 5-3, the acid resistance of the comparative pellet tablet 17 was reduced due to the degradation under accelerated stability conditions, which results in a reduction in the measured acid resistance value. The acid resistance value of pellet tablet 18 was also reduced due to the partial degradation of ilaprazole in the acceleration process. The pellet tablets A, G and H adopting the formula of the pellet core of the present invention can all demonstrate good acid resistance.

4.3 Effect of the Components of the Pellet Core Comprised in the Enteric-Coated Pellets on the Stability of the Enteric-Coated Pellet Tablets:

In the example 4.3, taking an ilaprazole enteric-coated pellet tablet as an example, the effects of the components of the pellet core comprised in the enteric pellets and the particle size of ilaprazole on their stability were compared.

Effect of the Components of the Pellet Core Comprised in the Enteric-Coated Pellets Comparison between the enteric-coated pellet tablet A according to the present invention and the comparative pellet tablets 11, 16 and 17 in terms of the stability In this example, the enteric-coated pellet tablet A according to the present invention and the comparative pellet tablets 11, 16 and 17 were subjected to the accelerated stability test. In this test, the pellet core of the comparative pellet tablet 11 does not comprise an alkaline compound and a surfactant, the pellet core of the comparative pellet tablet 16 does not comprise a surfactant but comprises an alkaline compound, and the pellet core of the comparative pellet tablet 17 does not comprise an alkaline compound but comprises a surfactant.

Test protocol: the enteric-coated pellet tablet A and the comparative pellet tablets 11 and 16 were packaged in HDPE bottles of 14 tablets respectively, and the packaged enteric-coated pellet tablets were placed in an accelerated stability test chamber at 40° C./RH75%, and sampled after 1/3/6 months for detecting related substances of the enteric-coated pellet tablets with different formulas. The stability data of the enteric-coated pellet tablets obtained by the test are shown in Table 6 below:

TABLE 6

Stability data of the enteric-coated pellet tablet A according to the present invention and the comparative pellet tablets 11, 16 and 17

| Time | Pellet tablet A | Comparative pellet tablet 11 | Comparative pellet tablet 16 | Comparative pellet tablet 17 |
|---|---|---|---|---|
| Day 0 | 0.12% | 0.23% | 0.26% | 1.54% |
| Month 1 | 0.15% | 0.89% | 0.57% | 3.25% |
| Month 3 | 0.36% | 1.69% | 0.86% | 6.26% |
| Month 6 | 0.87% | 2.76% | 1.05% | 8.12% |

As can be seen from the results shown in Table 6, when the pellet core in the ilaprazole enteric-coated pellet did not comprise an alkaline compound and a surfactant (i.e., the comparative pellet tablet 11), the enteric-coated pellet tablet cannot meet the stability requirement (the total impurity content should not exceed 1.5%); and when the pellet core of the ilaprazole enteric-coated pellet did not comprise an alkaline compound (i.e., the comparative pellet tablet 17), the content of the related substances was very high, more than 1.5%, in the freshly prepared pellet tablets. In contrast, the comparative pellet tablet 16 in which the pellet core comprised only an alkaline compound and did not comprise surfactants had good stability results for the accelerated test.

In summary, the stability requirement (i.e., the total impurity content should not exceed 1.5%) cannot be met for ilaprazole with low stability when its enteric-coated pellet tablet comprises only a water-insoluble alkaline compound in the first isolating layer (i.e., comparative pellet tablet 11); in addition, for the pellet tablet obtained when the pellet core does not comprise an alkaline compound but only a surfactant, the stability requirement cannot be met either.

4.3.2 Effect of the Particle Size of Ilaprazole in the Pellet Core Comprised in the Enteric-Coated Pellets on the Stability of the Enteric-Coated Pellet Tablets Comparison Between the Enteric-Coated Pellet Tablet A According to the Present Invention and the Comparative Pellet Tablets 3 and 4 in Terms of the Stability In this example, the enteric-coated pellet tablet A according to the present invention and the comparative pellet tablets 3 and 4 were subjected to the accelerated stability test. In this test, the particle size D90 of ilaprazole in the pellet core of the enteric-coated pellets in the comparative pellet tablet 3 were greater than or equal to 80 μm and less than or equal to 100 μm, and the particle size D90 of ilaprazole in the pellet core of the enteric-coated pellets in the comparative pellet tablet 4 is greater than 100 μm, compared to that in the enteric-coated pellet tablet A according to the present invention. The method is specified as follows:

Test protocol: the pellet tablet A and the pellet tablets 3 and 4 were packaged in HDPE bottles of 14 tablets respectively, and the packaged pellet tablets were placed in an accelerated stability test chamber at 40° C./RH75%, and sampled after 1/3/6 months for detecting related substances of the pellet tablets with different formulas. The stability data of the pellet tablets obtained by the test are shown in Table 7 below:

TABLE 7

Stability data of the enteric-coated pellet tablet A according to the present invention and the comparative pellet tablets 3 and 4

| Time | Pellet tablet A | Comparative pellet tablet 3 | Comparative pellet tablet 4 |
|---|---|---|---|
| Day 0 | 0.12% | 0.25% | 0.22% |
| Month 1 | 0.15% | 0.46% | 0.22% |
| Month 3 | 0.36% | 0.78% | 0.64% |
| Month 6 | 0.87% | 0.99% | 0.85% |

As can be seen from the results shown in Table 7, the stability of the comparative pellet tablets 3 (with the particle size D90 of ilaprazole greater than or equal to 80 μm and less than or equal to 100 μm) and 4 (with the particle size D90 of ilaprazole greater than 100 μm) comprising pellet cores with different particle sizes D90 of ilaprazole was still within the standard range (the total impurity content should not exceed 1.5%) compared to that of the enteric-coated pellet tablet A according to the present invention. That is, the change in the particle size D90 of ilaprazole comprised in the pellet core of the enteric-coated pellet does not affect the stability of the enteric-coated pellet tablet.

In summary, the particle size of ilaprazole comprised in the pellet core of the enteric-coated pellet does not affect the stability and the acid resistance of the enteric-coated pellet tablet prepared from the enteric-coated pellets.

4.4 Effect of the Protective Layer in the Enteric-Coated Pellets on the Stability and the Acid Resistance of the Enteric-Coated Pellet Tablets In this example, taking an ilaprazole enteric-coated pellet tablet as an example, the effects of the arrangement of the protective layer and the amount of its components in the enteric-coated pellets on the stability or acid resistance were compared.

4.4.1 Effect of the Arrangement of the Protective Layer in the Enteric-Coated Pellets 1) Comparison between the enteric-coated pellet tablet A according to the present invention and the comparative pellet tablet 12 in terms of the stability In this example, the enteric-coated pellet tablet A according to the present invention and the comparative pellet tablet 12 were subjected to the accelerated stability test. In this test, the enteric-coated pellets prepared into the comparative pellet tablet 12 did not comprise a protective layer.

Test protocol: the pellet tablet A and the pellet tablet 12 were packaged in HDPE bottles of 14 tablets respectively, and the packaged pellet tablets were placed in an accelerated stability test chamber at 40° C./RH75%, and sampled after 1/3/6 months for detecting related substances of the pellet tablets with different formulas. The stability data of the pellet tablets obtained by the test are shown in Table 8-1 below:

TABLE 8-1

Stability data of the pellet tablet A according to the present invention and the comparative pellet tablet 12

| Time | Pellet tablet A | Comparative pellet tablet 12 |
|---|---|---|
| Day 0 | 0.12% | 0.22% |
| Month 1 | 0.15% | 0.3% |
| Month 3 | 0.36% | 0.46% |
| Month 6 | 0.87% | 0.79% |

As can be seen from the results shown in Table 8-1, the stability of the comparative pellet tablet 12, in which the enteric-coated pellet does not comprise a protective layer, was still within the standard range (the total impurity content should not exceed 1.5%) compared to that of the enteric-coated pellet tablet A according to the present invention. That is, whether the enteric-coated pellet comprises a protective layer does not affect the stability of the enteric pellet tablet.

2) Comparison between the enteric-coated pellet tablet A according to the present invention and the comparative pellet tablet 12 in terms of the acid resistance In this example, the enteric-coated pellet tablet A according to the present invention and the comparative pellet tablet 12 were subjected to the acid resistance test. The acid resistance test described in section 4.2.1 was referred to for the specific method.

The results are shown in Table 8-2 below:

TABLE 8-2

Acid resistance data of the enteric-coated pellet tablet A according to the present invention and the comparative pellet tablet 12

| Time | Pellet tablet A | Comparative pellet tablet 12 |
|---|---|---|
| Day 0 | 96.7% | 88.4% |
| Month 1 | 95.9% | 87.5% |
| Month 3 | 95.5% | 87.3% |
| Month 6 | 95.3% | 86.4% |

As can be seen from Table 8-2, the acid resistance of the comparative pellet tablet 12 without a protective layer on the outside of the enteric coating layer was slightly lower than the standard range (i.e., the acid resistance average of 6 tablets should be not less than 90%). However, the inventors found in the experimental process that the lower acid resistance data of the determination was caused by the fact that the enteric-coated pellets without a protective layer were easy to adhere to each other, and part of the drug was degraded in the treatment process. Therefore, here, those skilled in the art will understand that if in the preparation of the enteric-coated pellet formulation, means other than providing a protective layer, such as timely mixing the formulation with a formulation excipient, can be provided to prevent the enteric-coated pellets from adhesion, whether to provide a protective layer will not affect the acid resistance of the formulation.

4.4.2 Effect of the Amount of the Components of the Protective Layer in the Enteric-Coated Pellets In this example, the enteric-coated pellet tablet A according to the present invention and the comparative pellet tablet 13 were tested and compared in terms of the acid resistance.

In this example, the enteric-coated pellet tablet A according to the present invention and the comparative pellet tablet 13 were subjected to the accelerated stability test. In this test, the content of the anti-adherent (such as magnesium stearate) in the protective layer of the enteric-coated pellets prepared into the comparative pellet tablet 13 was lower; for example, when the amount of ilaprazole was 5-15 parts, the amount of the anti-adherent was less than 0.5 parts.

Test protocol: the pellet tablet A and the pellet tablet 13 were packaged in HDPE bottles of 14 tablets respectively, and the packaged pellet tablets were placed in an accelerated stability test chamber at 40° C./RH75%, and sampled after 1/3/6 months for detecting the acid resistance of the pellet tablets, that is: the pellet tablet was dissolved in 0.1 M hydrochloric acid solution, and the pellets were collected after 2 h and detected for the content of the remaining ilaprazole. The acid resistance data of the pellet tablets obtained by the test are shown in Table 9 below:

TABLE 9

Acid resistance data of the enteric-coated pellet tablet A according to the present invention and the comparative pellet tablet 13

| Time | Pellet tablet A | Comparative pellet tablet 13 |
|---|---|---|
| Day 0 | 96.7% | 96.9% |
| Month 1 | 95.9% | 96.6% |
| Month 3 | 95.5% | 94.1% |
| Month 6 | 95.3% | 91.6% |

As can be seen from the results shown in Table 9, the acid resistance of the enteric-coated pellet tablet 13 also had a tendency to decrease after 6 months of the acceleration (i.e., from 96.9% at the beginning to 91.6% after 6 months) in the long-term test. The inventors found that, after 6 months of the acceleration, in the acid resistance test, part of the enteric-coated pellets of the comparative pellet tablet 13 adhered to the bottom of the dissolution cup, resulting in a decrease in the acid resistance. This indicates that when the amount of the water-insoluble inert material (such as talc, magnesium stearate and titanium dioxide) in the protective layer that is capable of preventing the pellets from adhesion is too low, the protective effect will be poor, and the enteric-coated pellets cannot be effectively prevented from adhesion, thereby affecting the acid resistance.

4.5 Dissolution Test of the Enteric-Coated Pellet Tablets 4.5.1 Comparison Between the Enteric-Coated Pellet Tablet A According to the Present Invention and the Comparative Pellet Tablet 15 in Terms of the Dissolution Rate In this example, the enteric-coated pellet tablet A according to the present invention and the comparative pellet tablet 15 were compared in terms of the dissolution rate according to the method described in section 4.1 above. The dissolution rate data of the pellet tablets obtained by the test are shown in Table 10 below:

TABLE 10

Dissolution rate data of the pellet tablet A according to the present invention and the comparative pellet tablet 15

| T/min | Pellet A | Comparative pellet tablet 15 |
|---|---|---|
| 0 | 0% | 0% |
| 10 | 35.80% | 34.5% |
| 15 | 68.50% | 66.3% |
| 20 | 82.90% | 80.1% |
| 30 | 95.20% | 94.2% |
| 45 | 94.30% | 93.8% |
| 60 | 92.20% | 91.5% |

As can be seen from the dissolution rate results shown in Table 10, both the enteric-coated pellet tablet A according to the present invention and the comparative pellet tablet 15 had good dissolution rate (the dissolution rate should be not less than 80%). This indicates that when the second isolating layer comprises only a binder, and does not comprise water-insoluble inert substance (e.g., an anti-adherent) that is capable of preventing the pellets from adhesion, the dissolution rate of the enteric-coated pellet formulation, and thus the in vivo bioavailability, will not be affected.

4.5.2 Comparison Between the Enteric-Coated Pellet Tablet A According to the Present Invention and the Comparative Pellet Tablets 7 and 8 in Terms of the Dissolution Rate In this example, the enteric-coated pellet tablet A according to the present invention and the comparative pellet tablets 7 and 8 were compared in terms of the dissolution rate according to the method described in section 4.1 above. The dissolution rate data of the pellet tablets obtained by the test are shown in Table 11 below and FIG. 1:

TABLE 11

Dissolution rate data of the pellet tablet A according to the present invention and the comparative pellet tablets 7 and 8

| T/min | Pellet A | Comparative pellet tablet 7 | Comparative pellet tablet 8 |
|---|---|---|---|
| 0 | 0% | 0% | 0% |
| 10 | 35.80% | 26.40% | 16.80% |
| 15 | 68.50% | 35.70% | 25.60% |
| 20 | 82.90% | 49.80% | 38.50% |
| 30 | 95.20% | 57.20% | 49.50% |
| 45 | 94.30% | 68.90% | 57.60% |
| 60 | 92.20% | 72.60% | 66.60% |

As can be seen from the dissolution rate results shown in FIG. 1 and Table 11, the enteric-coated pellet tablet A according to the present invention had good dissolution rate (the dissolution rate should be not less than 80%). The dissolution rates of the comparative pellets 7 and 8 were significantly lower than the required standard range (the dissolution rate should be not less than 80%) compared to that of the enteric-coated pellet tablet A according to the present invention, indicating that the release of these enteric-coated pellet tablets was significantly slowed down, which will delay the in vivo action, and thus affect the in vivo bioavailability.

As described above, the change in the proportions of components in the isolating layers of the enteric-coated pellet will not affect the stability and the acid resistance of the enteric-coated pellet tablet prepared from the enteric-coated pellets. However, the change in the proportions of the components in the isolating layer of the enteric-coated pellet will affect the dissolution rate of the corresponding enteric-coated pellet tablet, and thus affect the in vivo bioavailability of the formulation. Therefore, in order to further improve the in vivo bioavailability, according to the present invention, preferably, the proportions of the components in the isolating layer of the enteric-coated pellet can be: when the amount of ilaprazole is 5-15 parts, the first isolating layer comprises 5-36 parts of a binder and 5-36 parts of a water-insoluble alkaline compound, and the second isolating layer comprises 4-26 parts of a binder and 7-44 parts of a water-insoluble inert substance capable of preventing the pellets from adhesion.

4.5.3 Comparison Between the Enteric-Coated Pellet Tablet A According to the Present Invention and the Comparative Pellet Tablets 11 and 16 in Terms of the Dissolution Rate In this example, the enteric-coated pellet tablet A according to the present invention and the comparative pellet tablets 11 and 16 were compared in terms of the dissolution rate according to the method described in section 4.1 above. The dissolution rate data of the pellet tablets obtained by the test are shown in Table 12 below and FIG. 2:

TABLE 12

Dissolution rate data of the enteric-coated pellet tablet A according to the present invention and the comparative pellet tablets 11 and 16

| T/min | Pellet A | Comparative pellet 11 | Comparative pellet 16 |
|---|---|---|---|
| 0 | 0% | 0% | 0% |
| 10 | 35.8% | 22.5% | 29.5% |
| 15 | 68.5% | 27.6% | 46.3% |
| 20 | 82.9% | 37.2% | 66.6% |
| 30 | 95.2% | 45.4% | 78.3% |
| 45 | 94.3% | 51.6% | 81.8% |
| 60 | 92.2% | 60.5% | 83.9% |

Figure 2:
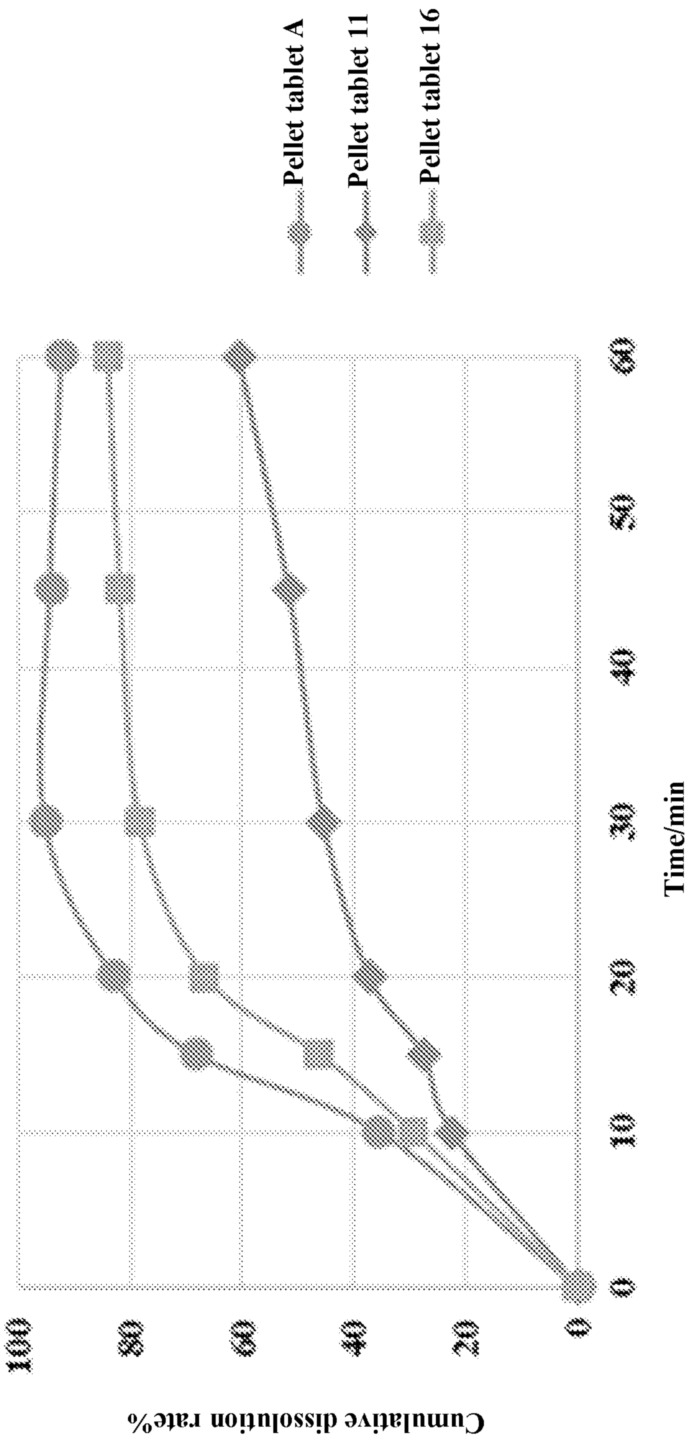
FIG. 2 is a graph of cumulative dissolution rates in an accelerated stability test of the pellet tablet according to the present invention versus comparative pellet tablets 11 and 16 (referred to as pellet tablets 11 and 16 in the figure) having different pellet core.

As can be seen from the results shown FIG. 2 and Table 12, the dissolution rate of the comparative pellet tablet 11 was significantly lower than the required standard (the dissolution rate should be not less than 80%) compared to that of the enteric-coated pellet tablet A according to the present invention.

In the comparative pellet tablet 16, the pellet core did not comprise a surfactant, and the drug dissolution rate of the formulation was within the standard range, but was lower than that of the enteric-coated pellet tablet A, and the dissolution rate was less than 85%.

As described above, the surfactant comprised in the pellet core of the enteric-coated pellet tablet will not affect the stability of the enteric-coated pellet tablet, but will affect the dissolution rate of the formulation. That is, the addition of the surfactant to the pellet core of the enteric-coated pellet tablet can effectively improve the dissolution rate of the formulation and thus the bioavailability.

4.5.4 Comparison Between the Enteric-Coated Pellet Tablet A According to the Present Invention and the Comparative Pellet Tablets 3 and 4 in Terms of the Dissolution Rate In this example, the enteric-coated pellet tablet A according to the present invention and the comparative pellet tablets 3 and 4 were compared in terms of the dissolution rate according to the method described in section 4.1 above. The dissolution rate data of the pellet tablets obtained by the test are shown in Table 13 below and FIG. 3:

TABLE 13

Dissolution rate data of the pellet tablet A according to the present invention and the comparative pellet tablets 3 and 4

| T/min | Pellet tablet A | Comparative pellet tablet 3 | Comparative pellet tablet 4 |
|---|---|---|---|
| 0 | 0% | 0% | 0% |
| 10 | 35.8% | 20.5% | 13.5% |
| 15 | 68.5% | 36.7% | 26.4% |
| 20 | 82.9% | 56.8% | 45.6% |
| 30 | 95.2% | 68.4% | 56.5% |
| 45 | 94.3% | 75.8% | 60.5% |
| 60 | 92.2% | 82.9% | 72.5% |

Figure 3:
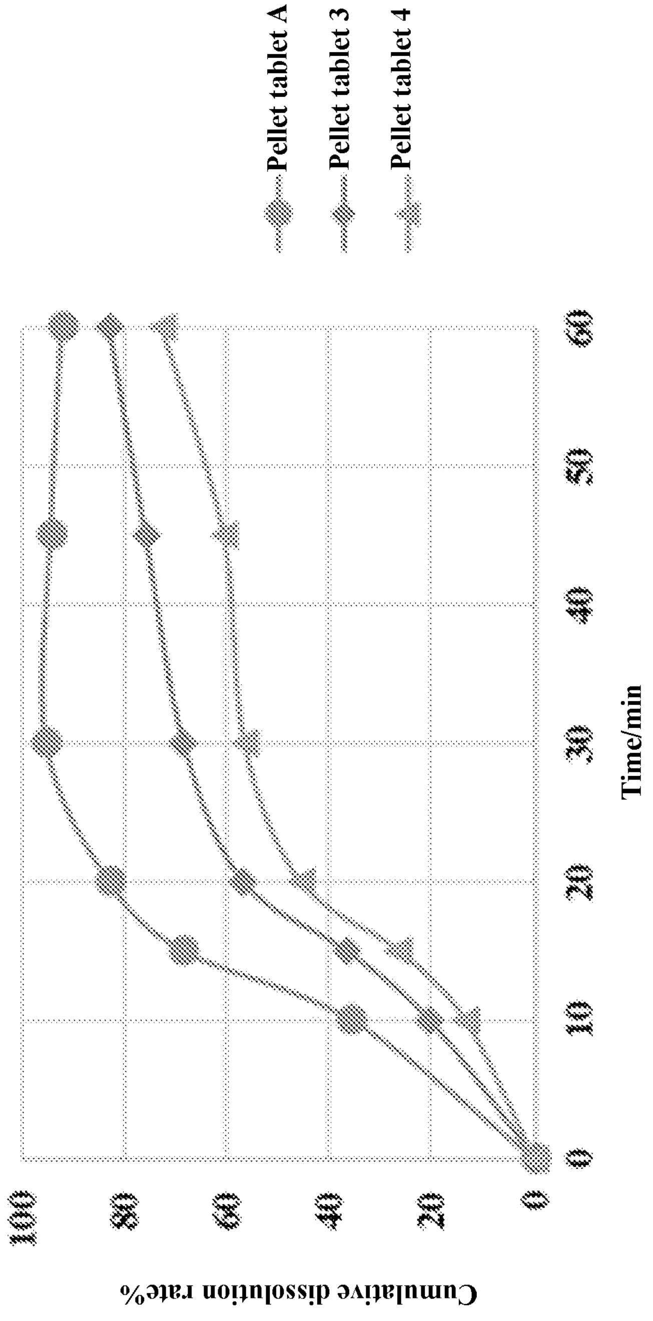
FIG. 3 is a graph of cumulative dissolution rates in an accelerated stability test of the pellet tablet according to the present invention versus comparative pellet tablets 3 and 4 (referred to as pellet tablets 3 and 4 in the figure) having different particle sizes of ilaprazole in pellet core formulas.

As can be seen from the dissolution rate results shown in FIG. 3 and Table 13, the dissolution rates of the comparative pellet tablets 3 and 4 were significantly reduced compared to that of the enteric-coated pellet tablet A according to the present invention, wherein when the particle size D90 of ilaprazole in the pellet core of the enteric-coated pellet was greater than 100 m (i.e., comparative pellet tablet 4), the dissolution rate was lower than the standard range (i.e., the dissolution rate should be not less than 80%).

4.5.5 Comparison Between the Enteric-Coated Pellet Tablet A According to the Present Invention and the Comparative Pellet Tablet 12 in Terms of the Dissolution Rate In this example, the enteric-coated pellet tablet A according to the present invention and the comparative pellet tablet 12 were compared in terms of the dissolution rate according to the method described in section 4.1 above. The dissolution rate data of the pellet tablets obtained by the test are shown in Table 14 below and FIG. 4:

TABLE 14

Dissolution rate data of the enteric-coated pellet tablet A according to the present invention and the comparative pellet tablet 12

| T/min | Pellet tablet A | Comparative pellet tablet 12 |
|---|---|---|
| 0 | 0% | 0% |
| 10 | 35.8% | 32.5% |
| 15 | 68.5% | 46.8% |
| 20 | 82.9% | 62.5% |
| 30 | 95.2% | 75.6% |
| 45 | 94.3% | 78.2% |
| 60 | 92.2% | 79.2% |

Figure 4:
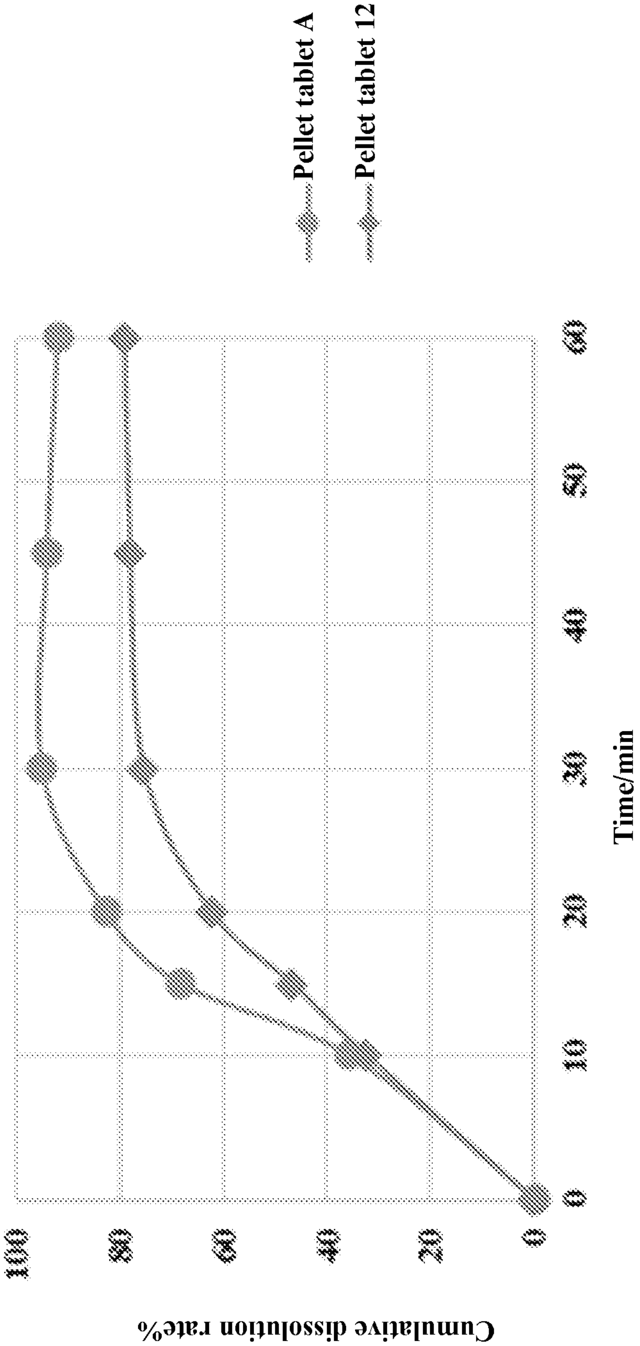
FIG. 4 is a graph of cumulative dissolution rates in an accelerated stability test of the pellet tablet according to the present invention versus a comparative pellet tablet 12 (referred to as a pellet tablet 12 in the figure) without a protective layer.

As can be seen from the results shown in FIG. 4 and Table 14, the dissolution rate of the comparative pellet tablet 12 without a protective layer was significantly reduced to about the standard value (the dissolution rate should be not less than 80%) compared to that of the enteric-coated pellet tablet A according to the present invention. The inventors found in the experiment that the significant decrease in the dissolution rate is caused by the fact that the enteric-coated pellets according to the present invention without a protective layer were easy to adhere to each other, thereby affecting the release rate in the dissolution medium. Therefore, the enteric-coated pellet tablet A having a protective layer will not generate the adhesion in the dissolution medium and thus has a higher release rate; while the comparative pellet tablet 12 having no protective layer will generate the adhesion in the medium and thus has a lower release rate. Therefore, here, those skilled in the art will understand that if in the preparation of the enteric-coated pellet formulation, means other than providing a protective layer, such as timely mixing the formulation with a formulation excipient, can be provided to prevent the enteric-coated pellets from adhesion, or if another isolation layer is added between the first isolating layer and the second isolating layer to prevent the enteric-coated pellets from easy adhesion, whether to provide a protective layer will not affect the dissolution rate of the formulation.

4.6 Effect of the Particle Size of Ilaprazole in the Pellet Core Comprised in the Enteric-Coated Pellets on the Drug-Loading Rate of the Enteric-Coated Pellet Tablets As can be seen from the comparison of the drug-containing pellet applying rates W (i.e., drug-loading rate) shown in the section "1.1 formula and method for preparing drug-containing pellet (W) and the drug-applying rate of the drug-containing pellet" in Example 1, the drug-loading rates $W_8$ and $W_9$ of the pellet cores W8 and W9 comprised in comparative pellet tablets 3 and 4 were 87.2% and 79.3%, respectively. In contrast, when the particle size D90 of ilaprazole comprised in the pellet core of the enteric-coated pellet tablet is ≤50 μm, the drug-loading rate of the pellet core (such as W1-W5) is more than 90%.

As described above, the particle size of ilaprazole comprised in the pellet core of the enteric-coated pellet does not affect the stability and the acid resistance of the enteric-coated pellet tablet prepared from the enteric-coated pellets; the particle size of ilaprazole comprised in the pellet core of the enteric-coated pellet will affect the dissolution rate of the enteric-coated pellet tablet, and thus affect the in vivo bioavailability. In addition, the particle size of ilaprazole comprised in the pellet core of the enteric-coated pellet will also affect the drug-loading rate of the pellet core of the enteric-coated pellet. Therefore, in order to further improve the in vivo bioavailability, preferably, the particle size D90 of ilaprazole in the pellet core of the enteric-coated pellet according to the present invention can be ≤100 m; more preferably, the particle size D90 of ilaprazole in the pellet core of the enteric-coated pellet according to the present invention can be 50 μm, and at this time, not only the drug release rate of the enteric-coated pellet tablet is relatively fast, i.e., the drug release rate reaches over 90% within 30 min, but also the pellet core has a higher drug-loading rate (greater than 90%).

Example 5. Acid-Inhibiting Effect of the Enteric-Coated Pellet Tablet According to the Present Invention Objective: To compare the acid-inhibiting effects of the enteric-coated pellet tablet A of the present invention and the comparative pellet tablets 1 and 2 on the first day of oral administration in healthy subjects.

Test protocol: the study was a randomized, open and cross-designed single-center study, with 18 healthy subjects enrolled. In one cycle of the test, 18 subjects were randomly divided into three groups of 6 persons, and the three groups were administered with the pellet tablet A, the comparative pellet tablet 1 and the comparative pellet tablet 2, respectively. Each person was administered with the drug once under fasting condition, and the intragastric pH was measured for 24 h.

Intragastric pH recording: intragastric pH was recorded with a pH testing system from Medtronic (Denmark). The catheter was placed in the stomach via the nasal cavity, with one end connected to a Digitrapper MKIII recording device. Intragastric pH of the subjects can be recorded continuously through a microprocessor in the recording device. The catheter was placed 8-10 cm away from the lower esophageal sphincter, with the scale on the surface of the catheter indicating its position. The probe was in the same position in each pH recording and had to be subjected to two-point calibration using pH 7.01 and pH 1.07 buffers before each pH monitoring. The data in the Digitrapper MKIII were downloaded to the computer for further analysis after each recording.

Figure 5:
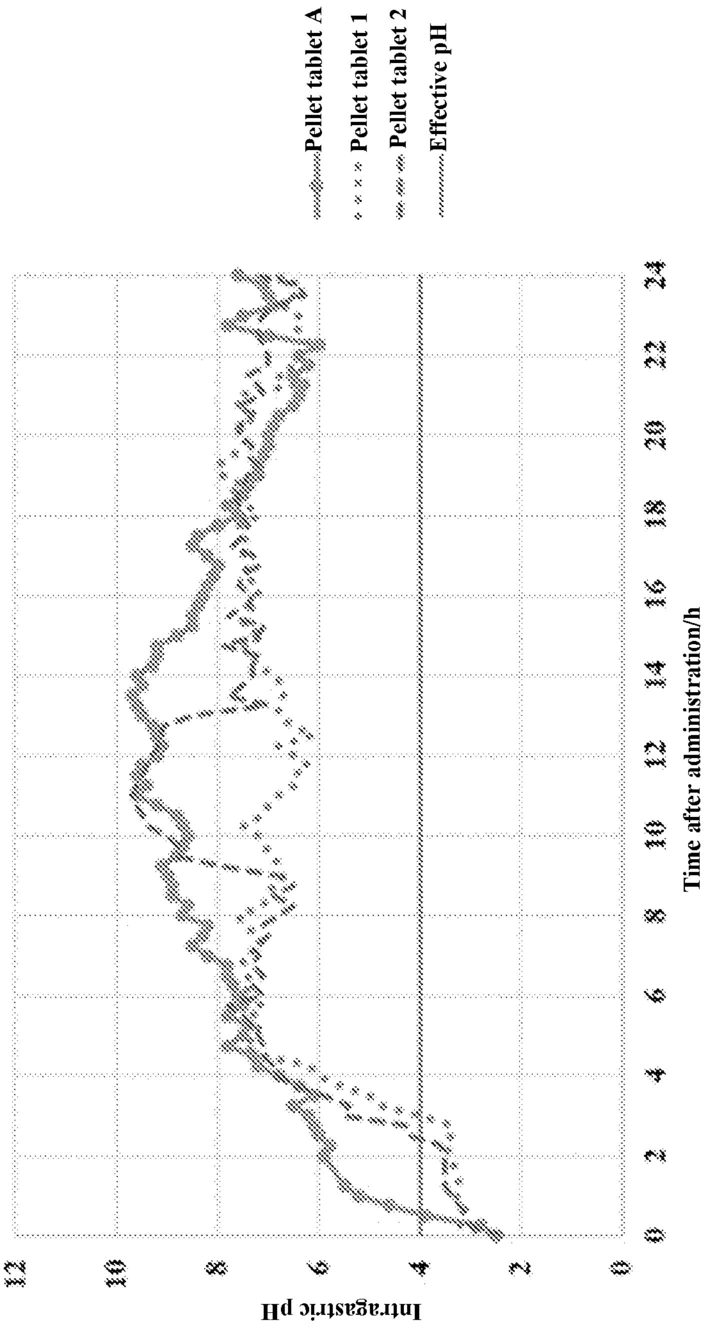
FIG. 5 is a graph of real-time human intragastric pH average recordings of the pellet tablet according to the present invention and the comparative pellet tablets 1 and 2 (referred to as pellet tablets 1 and 2 in the figure) prepared according to the method in the prior art.

Test results: the intragastric pH records of the subjects in each group were processed and the analyzed pH averages of a plurality of patients at each time point were plotted as a curve, as shown in FIG. 5.

As can be seen from FIG. 5, the enteric-coated pellet tablet A according to the present invention acted fast, inhibiting gastric acid to pH 4 or higher only within 1 h after the administration, thus achieving the clinical effect. Compared with the enteric-coated pellet tablet A according to the present invention, the comparative pellet tablet 1 achieved the clinical effect only about 3 h after the administration, and the comparative pellet tablet 2 achieved the clinical effect about 2.5 h after the administration. Therefore, the enteric-coated pellet tablet according to the present invention can achieve the effect quickly, thereby more quickly relieving patients' suffering.

In addition, in this example, the stability and acid resistance of the comparative pellet tablet 1 and the comparative pellet tablet 2 were also tested according to the methods in the above examples. The results are shown in Tables 15 and 16 below.

TABLE 15

Stability data of the comparative pellet tablet 1 and the comparative pellet tablet 2

| Time | Comparative pellet tablet 1 | Comparative pellet tablet 2 |
|---|---|---|
| Day 0 | 2.12% | 0.55% |
| Month 1 | 4.15% | 1.82% |
| Month 3 | 5.36% | 2.42% |
| Month 6 | 9.87% | 5.79% |

TABLE 16

Acid resistance data of the comparative pellet tablet 1 and the comparative pellet tablet 2

| Time | Comparative pellet tablet 1 | Comparative pellet tablet 2 |
|---|---|---|
| Day 0 | 92.6% | 90.1% |
| Month 1 | 88.3% | 85.5% |
| Month 3 | 83.5% | 81.3% |
| Month 6 | 80.6% | 78.9% |

As can be seen from Tables 15 and 16, the ilaprazole enteric-coated pellet tablets prepared according to the prior art (i.e., comparative pellet tablet 1 and comparative pellet tablet 2) had stability and acid resistance significantly lower than the required standards (stability standard: the total impurity should be not exceed 1.5%; acid resistance standard: the resistance should be no less than 90%) during the accelerated stability test.

Example 6. Pharmacokinetic Test of Ilaprazole Enteric-Coated Pellet Tablets According to the Present Invention in Beagle Dogs 1) Experimental design Test animals: beagle dogs.

Quantity: A total of 12 dogs, half male and half female, were divided into 3 groups (pellet tablet A, comparative pellet tablet 1 and comparative pellet tablet 2).

Administration mode and frequency: oral intragastric administration once (half an hour before the administration, 0.25 mg/mL pentagastrin was administered by intramuscular injection at a dose of 0.024 mL/kg).

Blood sampling points: 0 h before the administration, 1 h, 1.5 h, 1.75 h, 2 h, 2.5 h, 3 h, 3.5 h, 4 h, 5 h, 6 h and 8 h after the administration, for a total of 12 blood sampling points.

Dosage: single tablet.

2) Experimental period: single-tablet, three-cycle and three-crossover, and a washing period of 7 days, for a total of 15 days.

Administration regimens for beagle dogs were as follows:

| Beagle dog number | 1 | 2 | 3 | 4 | 5 | 6 | 7 | 8 | 9 | 10 | 11 | 12 |
|---|---|---|---|---|---|---|---|---|---|---|---|---|
| Cycle 1 | Pellet tablet A | Pellet tablet A | Pellet tablet A | Pellet tablet A | Pellet tablet 1 | Pellet tablet 1 | Pellet tablet 1 | Pellet tablet 1 | Pellet tablet 2 | Pellet tablet 2 | Pellet tablet 2 | Pellet tablet 2 |
| Cycle 2 | Pellet tablet 2 | Pellet tablet 2 | Pellet tablet 2 | Pellet tablet 2 | Pellet tablet A | Pellet tablet A | Pellet tablet A | Pellet tablet A | Pellet tablet 1 | Pellet tablet 1 | Pellet tablet 1 | Pellet tablet 1 |
| Cycle 3 | Pellet tablet 1 | Pellet tablet 1 | Pellet tablet 1 | Pellet tablet 1 | Pellet tablet 2 | Pellet tablet 2 | Pellet tablet 2 | Pellet tablet 2 | Pellet tablet A | Pellet tablet A | Pellet tablet A | Pellet tablet A |

3) Sample analysis: ilaprazole concentration in plasma was determined (plasma samples were treated with 1 mol/L NaOH solution to basify the plasma). Analysis method: HPLC-MS/MS.

Figure 6:
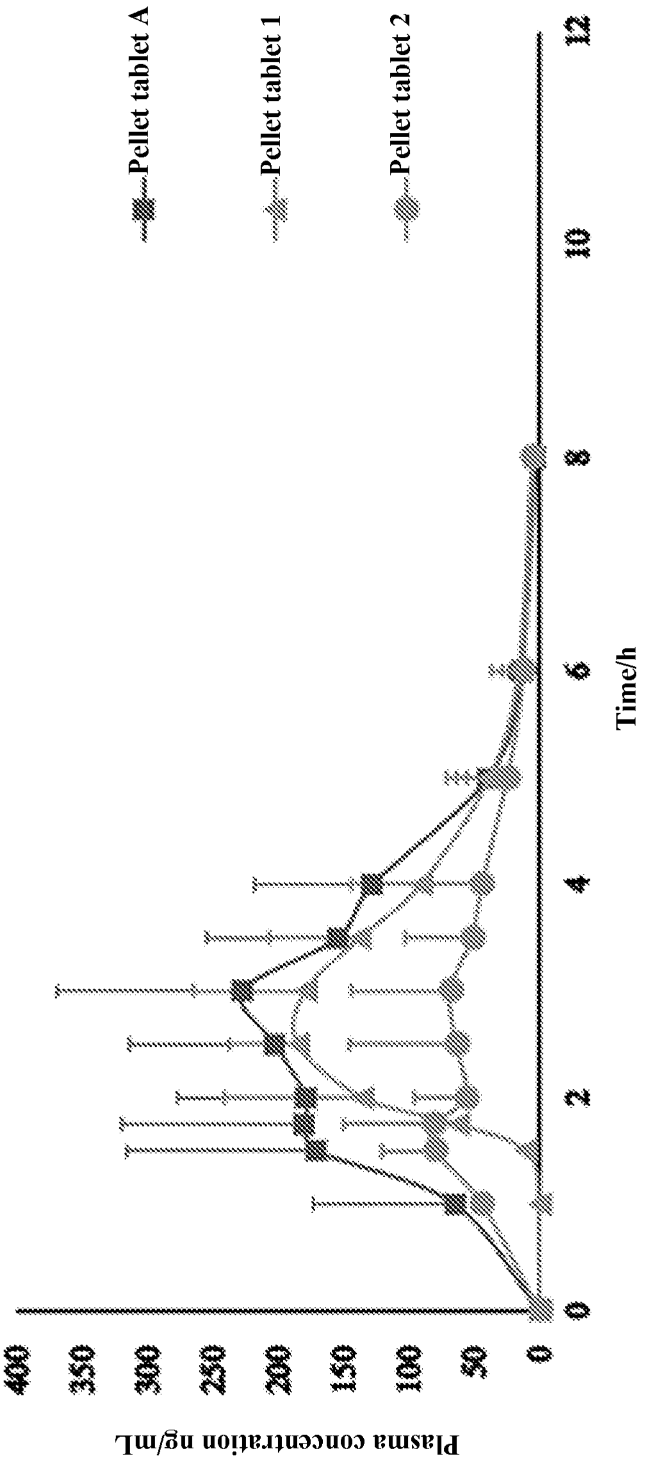
FIG. 6 is a graph of plasma concentration change curves in beagle dogs of the pellet tablet according to the present invention versus comparative pellet tablets 1 and 2 (referred to as pellet tablets 1 and 2 in the figure) prepared according to the method of the prior art.

4) Results: see FIG. 6.

As can be seen from the in vivo pharmacokinetic data plot of beagle dogs shown in FIG. 6, the enteric-coated pellet tablet A according to the present invention had higher bioavailability in beagle dogs and achieved the effect of inhibiting gastric acid secretion faster. In contrast, the comparative pellet tablet 1 and the comparative pellet tablet 2 had low cumulative plasma concentration in beagle dogs, indicating that the comparative pellet tablet 1 and the comparative pellet tablet 2 had low bioavailability.

Example 7. Comparison Between Prazoles in Terms of the Stability

Objective: To investigate the stability of different prazole starting materials in media at pH 6.8 and 8.0

Phosphate buffer media at pH 6.8 and 8.0 containing 0.5% w/w of sodium dodecyl sulfate were prepared, added into dissolution cups, with 1000 mL per cup. 0.5 mg of each of ilaprazole, omeprazole magnesium, esomeprazole magnesium, rabeprazole sodium, pantoprazole and lansoprazole was weighed and added into the dissolution cups, stirred at 150 rpm by a paddle method to ensure that the prazole starting materials sank into the media and dissolved therein. 5 mL of each of the samples was collected at 15 min, 30 min, 45 min and 60 min respectively, and added to 20 mL of sodium hydroxide stabilization medium, and then the volume was made up to 50 mL with the mobile phase.

The collected sample content in the media was determined according to the determination method of omeprazole magnesium, esomeprazole magnesium, rabeprazole sodium, pantoprazole sodium and lansoprazole in the *Chinese Pharmacopoeia* (Volume II, 2015 Edition) so as to determine the stability of the prazoles in the media at pH 6.8 and 8.0. The determination results are shown in Tables 17 and 18 below.

TABLE 17

The remaining amount of different prazoles after the degradation at different time points in medium at pH 6.8

| Time point | Ilaprazole | Omeprazole magnesium | Esomeprazole magnesium | Rabeprazole sodium | Pantoprazole sodium | Lansoprazole |
|---|---|---|---|---|---|---|
| 0 min | 100.0% | 100.0% | 100.0% | 100.0% | 100.0% | 100.0% |
| 15 min | 59.7% | 81.2% | 89.6% | 70.3% | 83.6% | 85.7% |
| 30 min | 42.7% | 66.7% | 70.9% | 51.5% | 65.9% | 70.2% |
| 45 min | 29.4% | 47.4% | 56.0% | 38.6% | 50.2% | 53.6% |
| 60 min | 20.7% | 29.2% | 41.4% | 24.6% | 35.4% | 38.6% |

TABLE 18

The remaining amount of different prazoles after the degradation at different time points in medium at pH 8.0

| Time point | Ilaprazole | Omeprazole magnesium | Esomeprazole magnesium | Rabeprazole sodium | Pantoprazole sodium | Lansoprazole |
|---|---|---|---|---|---|---|
| 0 min | 100.0% | 100.0% | 100.0% | 100.0% | 100.0% | 100.0% |
| 15 min | 94.3% | 98.2% | 99.2% | 97.3% | 98.6% | 98.7% |

TABLE 18-continued

| The remaining amount of different prazoles after the degradation at different time points in medium at pH 8.0 | | | | | | |
|---|---|---|---|---|---|---|
| Time point | Ilaprazole | Omeprazole magnesium | Esomeprazole magnesium | Rabeprazole sodium | Pantoprazole sodium | Lansoprazole |
| 30 min | 91.5% | 95.4% | 98.6% | 93.5% | 95.9% | 96.2% |
| 45 min | 88.6% | 96.3% | 97.6% | 90.6% | 92.2% | 95.3% |
| 60 min | 84.6% | 91.2% | 96.4% | 88.5% | 91.4% | 93.5% |

As can be seen from Tables 17 and 18, the stability of different prazoles in medium at pH 6.8 was relatively poor, wherein the stability of ilaprazole was the worst, and the stability of esomeprazole magnesium was the best.

Example 8. Preparation of Ilaprazole Pellet Dry Suspension

In this example, by taking the ilaprazole enteric-coated pellet according to the present invention as an example, the ilaprazole pellet dry suspension was prepared.

1) Formula of dry suspension granules V (unit: g)

| Components | Weight (g) |
|---|---|
| Xanthan gum | 20 |
| Chitosan | 1400 |
| CCNA | 75 |
| Aspartame | 15 |

Preparation method: xanthan gum, chitosan, CCNA and aspartame were mixed uniformly, and added to a dry granulator for granulation. Process parameters: pinch roller spacing: 0.2 mm, feeding speed: 30 rpm, pinch roller rotation speed: 5 rpm, and sizing rotation speed: 10 rpm. After granulation, the granules were sieved for sizing and the particle size was controlled to be 0.5-0.7 mm to obtain dry suspension granules V.

2) Preparation of dry suspensions E-V 60.5 mg of the ilaprazole enteric-coated pellets E and 2.0 g of the above dry suspension granules V were mixed and packaged in bottles to obtain the ilaprazole enteric-coated dry suspensions E-V with the specification of 5 mg.

The above examples only illustrate several embodiments of the present invention for the purpose of specific and detailed description, but should not be construed as limiting the scope of the present invention. It should be noted that various changes and modifications can be made by those skilled in the art without departing from the spirit of the present disclosure, and these changes and modifications are all within the scope of the present disclosure. Therefore, the protection scope of the present disclosure should be determined with reference to the appended claims.

The invention claimed is:

1. An enteric-coated pellet, comprising a pellet core, a first isolating layer, a second isolating layer, an enteric coating layer, and a protective layer in sequence from inside to outside, wherein, in parts by weight, the pellet core comprises: 5-15 parts of a blank pellet core, 5-15 parts of a drug-loading layer comprising: ilaprazole or a pharmaceutically acceptable salt thereof, 5-15 parts of a first water-insoluble alkaline compound as a first excipient, 0.2-0.6 parts of a surfactant, and 8-24 parts of a first binder;

the first isolating layer comprises 5-36 parts of a second binder and 5-36 parts of a second water-insoluble alkaline compound;

the second isolating layer comprises 4-26 parts of a third binder, and 7-44 parts of a first anti-adherent;

the enteric coating layer comprises 30-100 parts of an enteric coating material on a dry basis, 1-5 parts of a second anti-adherent, and 9-30 parts of a plasticizer; and the protective layer comprises 0.5-4 parts of a third binder, and 0.5-5 parts of a third anti-adherent, wherein:

the first and the second water-insoluble alkaline compounds are independently selected from one or more of magnesium hydroxide, magnesium oxide, magnesium carbonate, calcium carbonate, and calcium hydroxide;

the first, the second, and the third binder are independently selected from one or more of hydroxypropyl methylcellulose, hydroxypropylcellulose, polyvinylpyrrolidone, polyvinyl alcohol, methylcellulose, and polyethylene glycol;

the first, the second, and the third anti-adherent are independently selected from one or more of talc, magnesium stearate, titanium dioxide, and silica; and the protective layer is provided outside the enteric coating layer.

2. The enteric-coated pellet of claim 1, wherein the first water-insoluble alkaline compound and the second water-insoluble alkaline compound are the same or different.

3. The enteric-coated pellet of claim 1, wherein the ilaprazole and/or the pharmaceutically acceptable salt of ilaprazole has a particle size D90 of less than or equal to 100 μm, and the second isolating layer does not comprise an alkaline substance.

4. The enteric-coated pellet according to claim 1, wherein the pellet core and the first isolating layer are in contact with each other, and/or the first isolating layer and the second isolating layer are in contact with each other, and/or the second isolating layer and the enteric coating layer are in contact with each other.

5. The enteric-coated pellet according to claim 1, wherein the pharmaceutically acceptable salt of ilaprazole is selected from ilaprazole sodium, ilaprazole magnesium, ilaprazole zinc, ilaprazole potassium, ilaprazole lithium, and ilaprazole calcium.

6. The enteric-coated pellet according to claim 1, wherein the surfactant is tween-80 or sodium dodecyl sulfate.

7. The enteric-coated pellet according to claim 1, wherein the weight ratio of the second water-insoluble alkaline compound in the first isolating layer to ilaprazole and/or the pharmaceutically acceptable salt thereof is 0.3:1-3:1.

8. The enteric-coated pellet according to claim 1, wherein the weight ratio of the first anti-adherent to the third binder in the second isolating layer is in a range of 1-8:1.5-10, 1-10:1-20, or 4-26:7-44.

9. The enteric-coated pellet according to claim 2, wherein the particle size D90 of ilaprazole and/or the pharmaceutically acceptable salt of ilaprazole is in a range selected from the ranges consisting of any two of the following endpoints: 10 μm, 20 μm, 30 μm, 40 μm, 50 μm, 60 μm, 70 μm, 80 μm, 90 μm, and 100 μm.

10. A method for preparing the enteric-coated pellet according to claim 1, comprising the following steps:

1) preparing the pellet core comprising ilaprazole and/or the pharmaceutically acceptable salt of ilaprazole and the first excipient;

2) coating the first isolating layer and then coating the second isolating layer;

3) coating the enteric coating layer; and 4) coating the protective layer.

11. A pharmaceutical composition, selected from the enteric-coated pellet tablet comprising the enteric-coated pellet according to claim 1 and a second excipient and optionally a film coating, a capsule comprising the enteric-coated pellet having the protective layer, and a dry suspension comprising the enteric-coated pellet and dry suspension particles.

12. The enteric-coated pellet according to claim 1, wherein the weight ratio of the second water-insoluble alkaline compound of the first isolating layer to ilaprazole and/or the pharmaceutically acceptable salt thereof is 0.5:1-2:1, or 0.8:1-1.2:1.

13. The enteric-coated pellet according to claim 12, wherein the weight ratio of the second water-insoluble alkaline compound of the first isolating layer to ilaprazole and/or the pharmaceutically acceptable salt thereof is 1:1.

* * * * *